United States Patent
Ischakov et al.

(10) Patent No.: US 11,285,115 B2
(45) Date of Patent: Mar. 29, 2022

(54) PEPTIDE-BASED HYDROGEL PARTICLES AND USES THEREOF

(71) Applicant: Ramot at Tel-Aviv University Ltd., Tel-Aviv (IL)

(72) Inventors: Rafael Ischakov, Kiryat-Gat (IL); Ludmila Buzhansky, Ariel (IL); Lihi Adler-Abramovich, Herzlia (IL); Ehud Gazit, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 14/770,096

(22) PCT Filed: Feb. 27, 2014

(86) PCT No.: PCT/IL2014/050208
§ 371 (c)(1),
(2) Date: Aug. 25, 2015

(87) PCT Pub. No.: WO2014/132262
PCT Pub. Date: Sep. 4, 2014

(65) Prior Publication Data
US 2016/0008291 A1    Jan. 14, 2016

Related U.S. Application Data

(60) Provisional application No. 61/770,501, filed on Feb. 28, 2013.

(51) Int. Cl.
| | | |
|---|---|---|
| *A61K 38/05* | (2006.01) |
| *A61K 9/14* | (2006.01) |
| *A61K 9/19* | (2006.01) |
| *A61K 9/51* | (2006.01) |
| *B82Y 5/00* | (2011.01) |
| *C07K 5/065* | (2006.01) |
| *A61K 38/07* | (2006.01) |
| *A61K 38/08* | (2019.01) |
| *A61K 38/06* | (2006.01) |
| *A61K 38/12* | (2006.01) |
| *A61K 31/513* | (2006.01) |
| *A61K 31/704* | (2006.01) |
| *A61K 49/00* | (2006.01) |

(52) U.S. Cl.
CPC .......... *A61K 9/5123* (2013.01); *A61K 9/5192* (2013.01); *A61K 31/513* (2013.01); *A61K 31/704* (2013.01); *A61K 38/05* (2013.01); *A61K 38/06* (2013.01); *A61K 38/07* (2013.01); *A61K 38/08* (2013.01); *A61K 38/12* (2013.01); *A61K 49/0093* (2013.01); *B82Y 5/00* (2013.01); *C07K 5/06078* (2013.01)

(58) Field of Classification Search
None
See application file for complete search history.

(56) References Cited

U.S. PATENT DOCUMENTS

| | | | |
|---|---|---|---|
| 2008/0131509 A1 | 6/2008 | Hossainy et al. | |
| 2011/0008406 A1* | 1/2011 | Altman | A61K 38/1767 424/423 |
| 2011/0200675 A1* | 8/2011 | Thayumanavan | A61K 9/0019 424/487 |

FOREIGN PATENT DOCUMENTS

| | | |
|---|---|---|
| WO | WO 03/013474 | 2/2003 |
| WO | WO 2004/052773 | 6/2004 |
| WO | WO 2007/043048 | 4/2007 |
| WO | WO 2011/131671 | 10/2011 |
| WO | WO 2014/132262 | 9/2014 |

OTHER PUBLICATIONS

Orbach, Ron, et al. "Self-assembled Fmoc-peptides as a platform for the formation of nanostructures and hydrogels." Biomacromolecules 10.9 (2009): 2646-2651.*
Martin, Lee, et al. "The release of model macromolecules may be controlled by the hydrophobicity of palmitoyl glycol chitosan hydrogels." Journal of controlled release 80.1 (2002): 87-100.*
Chen, Wanyu, et al. "Formation of supramolecular hydrogel microspheres via microfluidics." Lab on a chip 9.20 (2009): 2947-2951. (Year: 2009).*
Moya-Ortega MD, Alvarez-Lorenzo C, Sigurdsson HH, Concheiro A, Loftsson T. Cross-linked hydroxypropyl-β-cyclodextrin and γ-cyclodextrin nanogels fordrug delivery: physicochemical and loading/release properties. Carbohydrate polymers. Feb. 14, 2012;87(3):2344-51. (Year: 2012).*
International Preliminary Report on Patentability dated Sep. 11, 2015 From the International Bureau of WIPO Re. Application No. PCT/IL2014/050208.
International Search Report and the Written Opinion dated Apr. 30, 2014 From the International Searching Authority Re. Application No. PCT/IL2014/050208.
Abismail et al. "Emulsification by Ultrasound: Drop Size Distribution and Stability", Ultrasonics Sonochemistry, 6: 75-83, 1999.
Adhikari et al. "Self-Assembled Peptides: From Molecules to Nanobiomaterials", Journal of the Indian Institute of Science, 91(4): 471-483, Oct.-Dec. 2011.
Alam et al. "Novel Dipeptide Nanoparticles for Effective Curcumin Delivery", International Journal of Nanomedicine, 7: 4207-4222, 2012.
Bawa et al. "Self-Assembling Peptide-Based Nanoparticles Enhance Cellular Delivery of the Hydrophobic Anticancer Drug Ellipticine Through Caveolae-Dependent Endocytosis", Nanomedicine: Nanotechnology, Biology, and Medicine, NBM, 8: 647-654, 2012.

(Continued)

*Primary Examiner* — Nissa M Westerberg

(57) ABSTRACT

Compositions comprising self-assembled hydrogel particles formed of short peptides which comprise one or more aromatic amino acid residue(s) in an inverted emulsion are disclosed. Such hydrogel particles which encapsulate an active agent and uses thereof in therapeutic and diagnostic applications are also disclosed.

24 Claims, 9 Drawing Sheets
Specification includes a Sequence Listing.

(56) References Cited

OTHER PUBLICATIONS

Feng et al. "Vitamin E TPGS-Emulsified Poly(Lactic-Co-Glycolic Acid) Nanoparticles for Cardiovascular Restenosis Treatment", Nanomedicine, 2(3): 333-344, Jun. 2007. Abstract.

Goncalves et al. "Self-Assembled Hydrogel Nanoparticles for Drug Delivery Applications", Materials, 3: 1420-1460, Feb. 24, 2010.

Hecht et al. "Surfactant Concentration Regime in Miniemulsion Polymerization for the Formation of MMA Nanodroplets by High-Pressure Homogenization", Langmuir, 27: 2279-2285, Feb. 11, 2011.

Ischakov et al. "Peptide-Based Hydrogel Nanoparticles as Effective Drug Delivery Agents", Bioorganic & Medicinal Chemistry, 21(12): 3517-3522, Jun. 15, 2013. Abstract. Abstract.

Mahler et al. "Rigid, Self-Assembled Hydrogel Composed of A Modified Aromatic Dipeptide", Advanced Materials, 18: 1365-1370, 2006.

Mu et al. "Vitamin E TPGS Used as Emulsifier in the Solvent Evapoation/Extraction Technique for Fabrication of Polymeric Nanospheres for Controlled Release of Paclitaxel (Taxol®)", Journal of Controlled Release, 80: 129-144, 2002.

Myers "Overview", Surfactant Science and Technology, 3rd. Ed., 169 P., 2006.

Na et al. "Self-Assembled Hydrogel Nanoparticles From Curdlan Derivatives: Characterization, Anti-Cancer Drug Release and Interaction With A Hepatoma Cell Line (HepG2)", Journal of Controlled Release, 69: 225-236, 2000.

Orbach et al. "Self-Assembled Fmoc-Peptides as A Platform for the Formation of Nanostructures and Hydrogels", Biomacromolecules, 10(9): 2646-2651, Sep. 2009. Abstract. Abstract.

Orbach et al. "Self-Assembled Fmoc-Peptides as A Platform for the Formation of Nanostructures and Hydrogels", Biomacromolecules, 10: 2646-2651, 2009.

Sasaki et al. "Nanogel Engineering for New Nanobiomaterials: From Chaperoning Engineering to Biomedical Applications", The Chemical Record, 10: 366-376, 2010.

Supplementary European Search Report and the European Search Opinion dated Oct. 31, 2016 From the European Patent Office Re. Application No. 14757294.5. (10 Pages).

Orbach el al. "The Rheological and Structural Properties of Fmoc-Peptide-Based Hydrogels: The Effect of Aromatic Molecular Architecture on Self-Assembly and Physical Charactcristics", Langmuir, XP055313227, 28(4): 2015-2022, Jan. 5, 2012. p. 2015, 1-h col., Line 13-r-h col., Line 21, p. 2021, r-h col., Para Conclusions, Fig. 1.

* cited by examiner

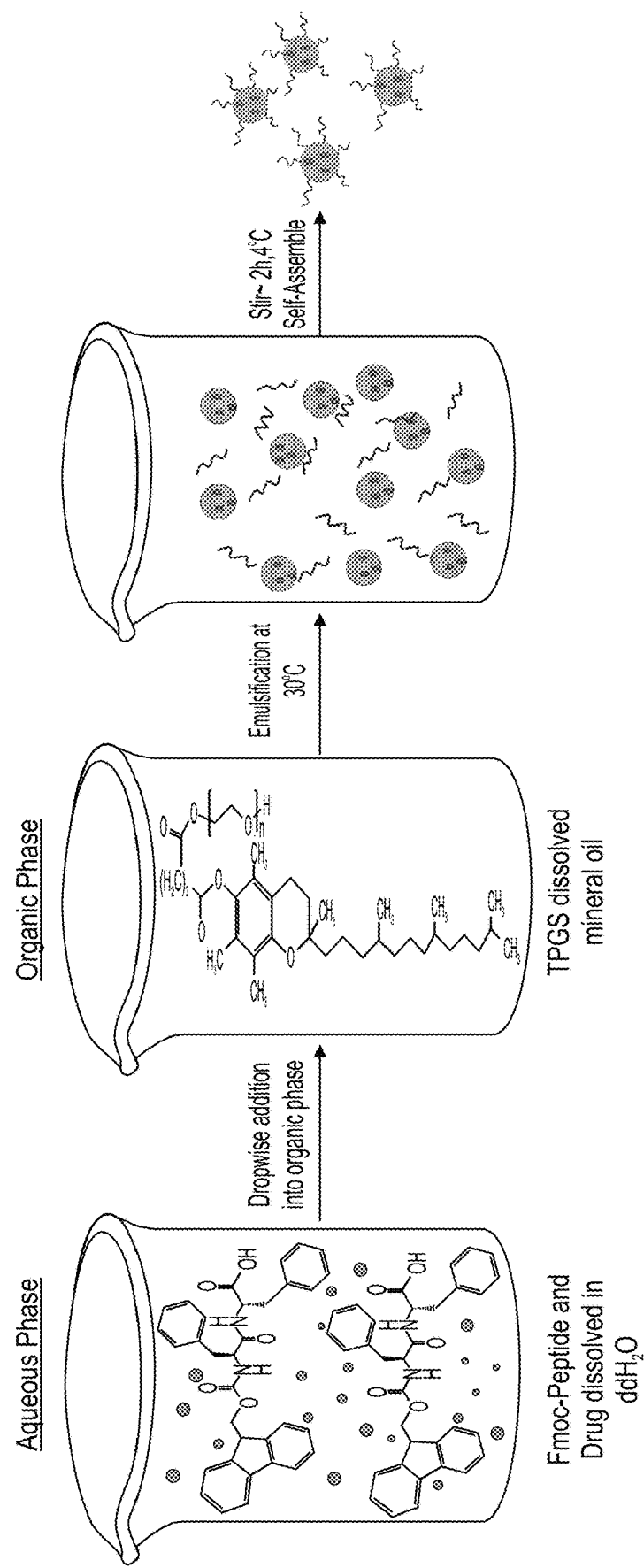
FIG. 1A -Continued

Aggregated HNPs before their suspension in PBS

HNPs after their suspension in PBS

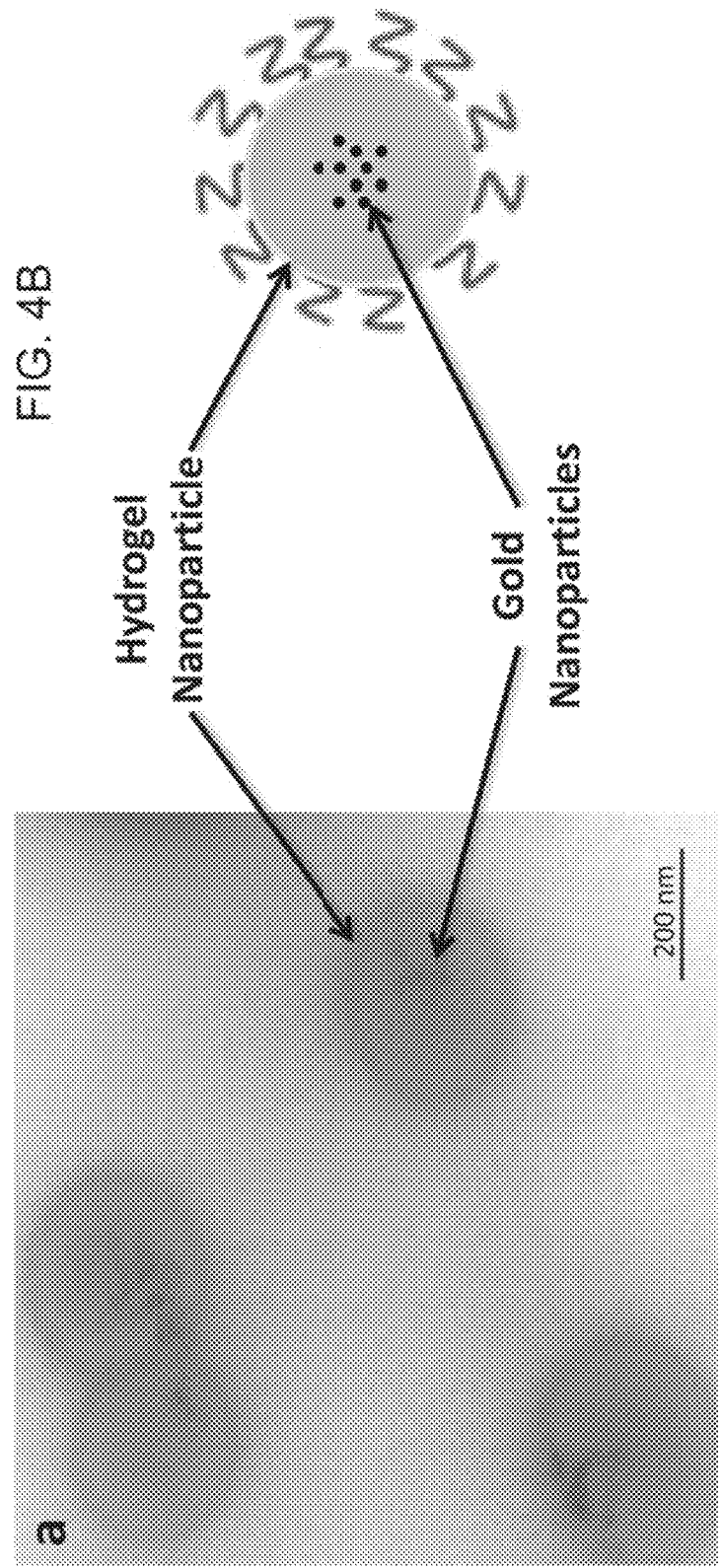

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: may have  N-terminus capping modification such
      as 9-fluorenylmethyloxycarbonyl (Fmoc) or other moieties.

<400> SEQUENCE: 1

Phe Arg Gly Asp
1

PEPTIDE-BASED HYDROGEL PARTICLES AND USES THEREOF

RELATED APPLICATIONS

This application is a National Phase of PCT Patent Application No. PCT/IL2014/050208 having International filing date of Feb. 27, 2014, which claims the benefit of priority under 35 USC § 119(e) of U.S. Provisional Patent Application No. 61/770,501 filed on Feb. 28, 2013. The contents of the above applications are all incorporated by reference as if fully set forth herein in their entirety.

FIELD AND BACKGROUND OF THE INVENTION

The present invention, in some embodiments thereof, relates to nanotechnology and, more particularly, but not exclusively, to novel peptide-based hydrogel particles and uses thereof in medicinal applications as, for example, nanocarriers for drug delivery.

Nanotechnology is an emerging multidisciplinary field promising to provide solutions and improve the pharmacokinetic and pharmacodynamic properties of various types (e.g., water soluble/insoluble) of bioactive agents. The promise of nanotechnology lies in the ability to engineer customizable nanoscale constructs that can be loaded with one or more payloads and deliver them to the target site.

In general, nanoparticles that are used in biomedical applications should exhibit the following parameters: (i) synthesis of the NPs should be facile and reproducible (e.g., involve non-complicated techniques, and avoid multi-step synthetic pathway); (ii) synthesis conditions of the NPs should allow encapsulation of various types of bioactive agents with high yield and should be devoid of chemical reactions that may affect the biological activity of the encapsulated entities; (iii) size and surface properties of the NPs should be controllable, for achieving both active and passive targeting while avoiding recognition and rapid clearance by the reticuloendothelial system; and (iv) NPs should display properties favorable for controlled and/or sustained release of the bioactive agent at the target site and for improving pharmacokinetic properties of the encapsulated entities [MacKay et al. *Nat. Mater.* 2009, 8, 993-999; Gonçalves et al. *Materials* 2010, 3, 1420-1460].

Currently practiced methodologies for the preparation of nanoparticles utilize polymers such as polylactic acid or poly(lactic-co-glycolic acid) (PLGA), phospholipids (liposomes), and organic-inorganic composite particles.

Polymer-based hydrogel nanoparticles (HNPs) have been recently described as effective drug delivery vehicles [Gonçalves et al. *Materials* 2010, 3, 1420-1460]. Similar to conventional bulk hydrogels, HNPs are moldable, environmentally friendly, easily synthesized, soft, elastic and biocompatible materials which include high content (85-99%) of water or an aqueous solution [Gonçalves et al. *Materials* 2010, 3, 1420-1460].

Hydrogel nanostructures exhibit properties suitable for the drug transfer of water-soluble bioactive substances such as, for example, small drug molecules, as well as high molecular weight macromolecules such as peptides, proteins, siRNA and DNA.

Various types of synthetic polymers (e.g., polyvinyl alcohol and polyethylene oxide) and natural polymers (e.g., chitosan and gelatin) have been suggested for use as building blocks for HNPs formation. However, HNPs prepared from such polymers often involve complicated synthetic techniques, including, for example, extreme temperatures and pHs, and often require use of chemicals that adversely affect the biocompatibility of the obtained HNPs.

Natural or synthetic self-assembled peptides represent an additional type of gel forming molecules [Roli et al. *Nanomed. Nanotech. Biol.* 2012, 8, 647-654; Adhikari and Arindam, *J. Indian Inst. Sci.* 2011, 91, 471-483].

Orbach et al. [in *Biomacromolecules* 2009, 10, 2646-2651], Mahler et al. [in *Adv. Mater.* 2006, 18, 1365-1370], as well as WO 2007/043048, have reported that aromatic dipeptides such as N-fluorenylmethoxycarbonyl-diphenylalanine (Fmoc-FF), self-assemble in aqueous solutions to form nano-scale ordered hydrogels of remarkable mechanical rigidity.

Additional background art includes Alam et al., *Int J Nanomedicine.* 2012; 7: 4207-4222; Abismail, et al. *Ultrason. Sonochem.* 1999, 6, 75-83]; Mua, and Feng, *J. Contr. Release* 2002, 80, 129-144; Feng et al. *Nanomedicine* 2007, 2, 333-344; Myers, D. *Surfactant Science and Technology*. New York: VCH, 1988; Yoshihiro and Akiyoshi, K. *Chem. Rec.* 2010, 10, 366-376; Hecht et al. *Langmuir* 2011, 27, 2279-2285.

SUMMARY OF THE INVENTION

The present inventors have now designed and successfully practiced a scalable process for the self-assembly of peptides (e.g., aromatic dipeptides) into hydrogel particles, such as hydrogel nanoparticles (HNPs), which can be efficiently utilized, for example, as carriers for delivery of bioactive agents for therapeutic and diagnostic applications.

In the therapeutic field, hydrogel particles as described herein can serve as vectors for delivering of hydrophilic and hydrophobic bioactive substances: small drug molecules, as well as high molecular weight biomolecules such as peptides, proteins, siRNA and DNA. In the diagnostic field, the hydrogel particles described herein can be loaded with imaging agents such as magnetic or gold nanoparticles and serve as a potent biocompatible diagnostic tool for broad range of diseases.

The hydrogel particles can be modified with any type of biological or synthetic molecule to improve stability, efficiency and/or bioavailability.

According to an aspect of some embodiments of the present invention there is provided a composition comprising a plurality of physically discrete hydrogel particles, each hydrogel particle comprising a three-dimensional network made of a plurality of self-assembled peptides and an aqueous medium, wherein each peptide in the plurality of peptides comprises 2-6 amino acid residues, at least one of the amino acids being an aromatic amino acid.

According to some embodiments of the invention, the hydrogel particles are nanoparticles.

According to some embodiments of the invention, an average diameter of each of the hydrogel particles ranges from 10 nm to 1000 nm, or from 10 nm to 500 nm.

According to some embodiments of the invention, the plurality of peptides comprises a plurality of dipeptides.

According to some embodiments of the invention, at least one of the plurality of dipeptides is an aromatic-homodipeptide.

According to some embodiments of the invention, each peptide in the plurality of dipeptides is an aromatic-homodipeptide.

According to some embodiments of the invention, the plurality of aromatic dipeptides comprises a plurality of diphenylalanine peptides.

According to some embodiments of the invention, at least one of the peptides comprises a RGD sequence.

According to some embodiments of the invention, each peptide in the plurality of peptides comprises an RGD sequence.

According to some of any of the embodiments of the invention, at least one of the peptides comprises an end-capped moiety.

According to some of any of the embodiments of the invention, each of the peptides comprises an end-capped moiety.

According to some of any of the embodiments of the invention, the end-capping moiety is an aromatic end-capping moiety.

According to some of any of the embodiments of the invention, the end-capping moiety substitutes an N-terminus of the dipeptide.

According to some of any of the embodiments of the invention, the end-capping moiety is 9-fluorenylmethyloxy-carbonyl (Fmoc).

According to some of any of the embodiments of the invention, the plurality of peptides comprises a plurality of diphenylalanine peptides having an end-capping moiety substituting the N-terminus thereof.

According to some of any of the embodiments of the invention, each of the diphenylalanine peptide is an Fmoc-diphenylalanine (Fmoc-FF) peptide.

According to some of any of the embodiments of the invention, the plurality of peptides comprises a plurality of peptides having an FRGD sequence as set forth in SEQ ID NO:1 and an end-capping moiety substituting the N-terminus thereof.

According to some of any of the embodiments of the invention, each of the diphenylalanine peptide is an Fmoc-diphenylalanine (Fmoc-FF) peptide.

According to some of any of the embodiments of the invention, the hydrogel particles are formed upon self-assembling the plurality of peptides in an inverted emulsion.

According to some of any of the embodiments of the invention, the inverted emulsion comprises an emulsion stabilizer.

According to some of any of the embodiments of the invention, the further comprises an emulsion stabilizer being in association with the particles.

According to some of any of the embodiments of the invention, the emulsion stabilizer is a Vitamin E derivative.

According to some of any of the embodiments of the invention, the vitamin E derivative is vitamin E-TPGS.

According to some of any of the embodiments of the invention, a composition as described herein is prepared by:

adding an aqueous solution comprising the plurality of peptides to an organic solution, to thereby form an inverted (water-in-oil) emulsion; and subjecting the emulsion to high speed homogenization.

According to some of any of the embodiments of the invention, at least a portion of the hydrogel particles have a moiety or an agent incorporated therein and/or associated therewith.

According to some of any of the embodiments of the invention, the agent is a bioactive agent selected from the group consisting of a diagnostic agent and a therapeutically active agent.

According to some of any of the embodiments of the invention, the composition is in a form of a dry powder.

According to some of any of the embodiments of the invention, composition further comprises a cryoprotectant.

According to some of any of the embodiments of the invention, the further comprises a pharmaceutically acceptable carrier.

According to some of any of the embodiments of the invention, the composition is usable for systemic administration.

According to an aspect of some embodiments of the present invention there is provided a process of preparing the composition of any of the embodiments described herein, the process comprising:

adding an aqueous solution comprising the plurality of peptides to an organic solution, to thereby form an inverted (water-in-oil) emulsion; and subjecting the emulsion to high speed homogenization.

According to some of any of the embodiments of the invention, the aqueous solution of the peptides is formed by diluting a solution of the plurality of peptides and a water-miscible organic solvent in an aqueous solution.

According to some of any of the embodiments of the invention, the homogenization is performed at a speed rate of at least 10,000 rpm.

According to some of any of the embodiments of the invention, the inverted emulsion further comprises an emulsion stabilizing agent, as described herein.

According to some of any of the embodiments of the invention, the process further comprises isolating the hydrogel particles from the emulsion.

According to some of any of the embodiments of the invention, the process further comprises subjecting the hydrogel particles to lyophilization.

According to some of any of the embodiments of the invention, the lyophilization is effected in the presence of a cryoprotecting agent.

According to some of any of the embodiments of the invention, the hydrogel particles further comprise a bioactive agent incorporated therein, the process further comprising, prior to adding the aqueous solution of peptides to the organic solution, adding the bioactive agent to the aqueous solution of the peptides.

According to an aspect of some embodiments of the present invention there is provided a composition comprising a bioactive agent as described herein, for use in delivering the bioactive agent to a bodily organ or tissue.

According to an aspect of some embodiments of the present invention there is provided a use of composition comprising a bioactive agent as described herein, for in the manufacturing of a delivery system or a carrier for delivering the bioactive agent to a bodily organ or tissue.

According to an aspect of some embodiments of the present invention there is provided a method of delivering a bioactive agent to a bodily organ or tissue of a subject, the method comprising administering to the subject a composition comprising a bioactive agent as described herein.

According to some of any of the embodiments of the invention, the delivering is effected via systemic administration.

According to some of any of the embodiments of the invention, the bioactive agent is a therapeutically active agent, the composition being for use in treating a medical condition treatable by the bioactive agent.

According to some of any of the embodiments of the invention, the bioactive agent is a diagnostic agent, the composition being for use in monitoring a medical condition for which the diagnostic agent is indicative.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-B present a TEM image of gold nanoparticle clusters encapsulated by exemplary HNPs, made of Fmoc-FF according to some embodiments of the present invention (FIG. 4A) and a schematic illustration of gold nanoparticles-encapsulating HNPs, according to exemplary embodiments of the present invention (FIG. 4B);

DESCRIPTION OF SPECIFIC EMBODIMENTS OF THE INVENTION

Figure 1A:
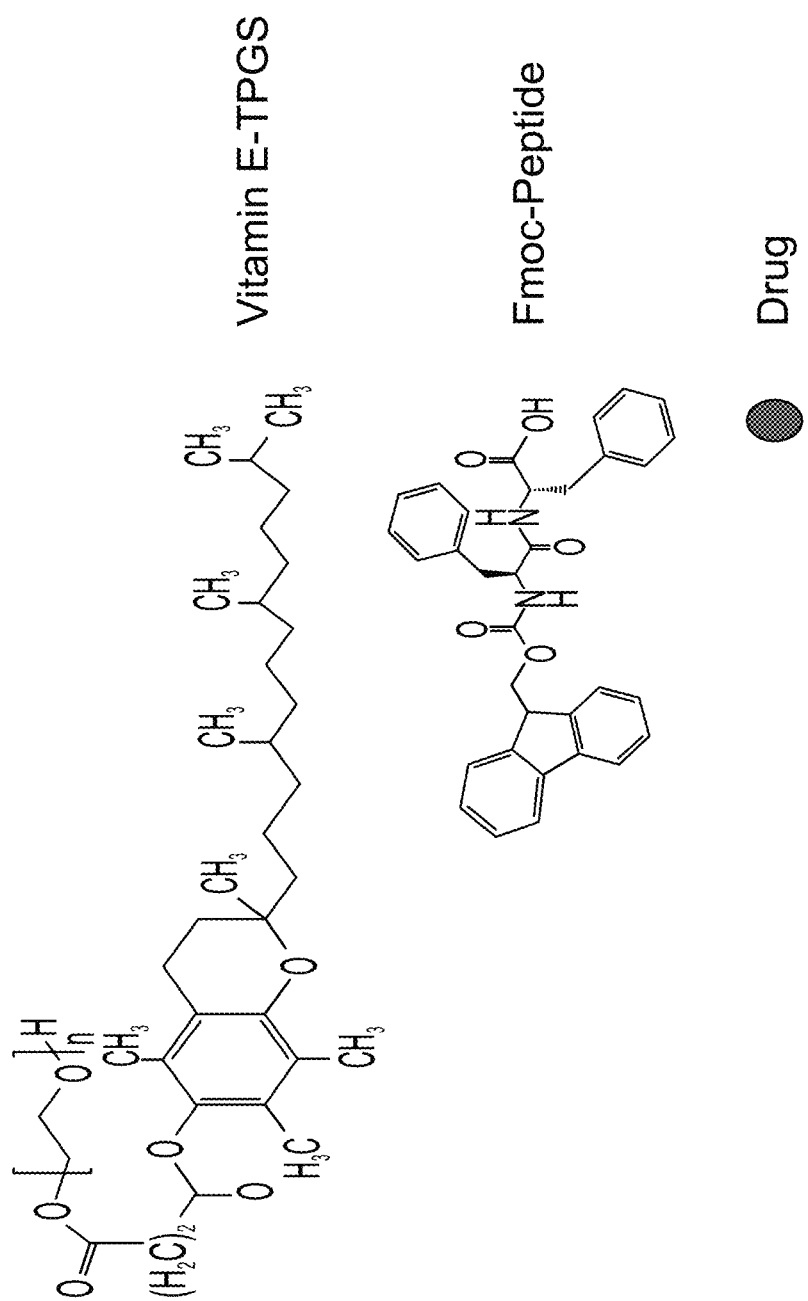
FIGS. 1A-D present a schematic illustration of a process of preparing drug-encapsulating HNPs made of Fmoc-FF by modified inverse emulsion method according to exemplary embodiments of the present invention (FIG. 1A), a TEM image of exemplary HNPs made of Fmoc-FF according to some embodiments of the present invention (FIG. 1B), a comparative background art TEM image of a fibirllar hydrogel made of Fmoc-FF diluted in aqueous solution, as described in Mahler et al. 2006, supra (FIG. 1C) and a size distribution curve of exemplary NHPs according to some embodiments of the present invention, as measured by dynamic light scattering (DLS) (FIG. 1D)

The present invention, in some embodiments thereof, relates to nanotechnology and, more particularly, but not exclusively, to novel peptide-based hydrogel particles and uses thereof in medicinal as well as other applications, for example as nanocarriers for drug delivery.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Peptide-based HNPs exhibit numerous advantages over polymeric hydrogel nanoparticles: (i) formation of peptide-based HNPs through molecular self-assembly avoids the need to use potentially hazardous chemicals that may affect biocompatibility; (ii) peptide-based HNPs typically biodegrade into non-toxic metabolites, since the building blocks of the HNPs are peptides composed of simple (e.g., naturally-occurring) amino acids; and (iii) short peptide building blocks are easy to manufacture in large quantities.

In addition, HNPs can be decorated chemically and biologically.

Thus, peptide-based HNP scaffolds represent an important biocompatible group of materials which exhibit the advantages of both synthetic and naturally derived hydrogel forming materials. They are easy to manufacture in large quantities and can also be easily decorated chemically and biologically, giving the ability to design an ultrastructure with, for example, improved targeting and prolonged in vivo stability, and/or other functionalities.

Such decoration gives, for example, the ability to design hydrogel nanoparticles with improved targeting ability. Furthermore, when used as nanocarriers, the HNPs can be designed to allow a controlled and sustained release of a bioactive agent from the matrix of the nanoparticle at the target site, improving bioavailability and reduction dosing frequency of the bioactive molecule.

The present inventors have devised and successfully practiced a novel methodology in which hydrogel particles (e.g., hydrogel microparticles and/or nanoparticles) are formed from aromatic peptides (e.g., aromatic dipeptides). These hydrogel particles, which are collectively referred to herein as hydrogel nanoparticles (HNPs), were prepared by utilizing mechanical homogenization and inverse-emulsion methods, with the aim of serving as nanocarriers for controlled drug delivery.

As shown in the Examples section that follows, Fmoc-FF based and Fmoc-FRGD (Fmoc-capped peptide having an amino acid sequence as set forth in SEQ ID NO:1) based nanoparticles were formed using inverse (or inverted) emulsion technique. In order to stabilize those NPs in aqueous solutions, D-α-tocopheryl, polyethylene glycol 1000 succinate (vitamin E-TPGS), as a biocompatible and biodegradable surfactant, was applied. In order to define the most favorable conditions for HNPs formulation, a series of parameters was evaluated and examined with respect to physical stability in physiological buffer; size and zeta potential; post-formulation modifications for prolonged shelf-life; encapsulation efficiency and controlled drug release kinetics.

As demonstrated in the Examples section that follows, exemplary such HNPs were prepared from Fmoc-FF, formulated via modified inverse-emulsion method using vitamin E-TPGS as an exemplary emulsion stabilizer and high speed homogenization. Nanoparticles formation was demonstrated by TEM analyses. The formed HNPs exhibited two distinguishable populations having an average size of 21.5±1.3 nm and 225.9±0.8 nm, and were shown to controllably release small molecules such as the anti-cancer drugs Doxorubicin and 5-FU. Encapsulation of DNA was also demonstrated. HNPs prepared from RGD-containing short peptides was also demonstrated.

The overall results suggest that the physical and chemical properties of the obtained HNPs represent a novel platform for drug delivery application and other bionanotechnological applications.

These results further clearly indicate that aromatic peptide-based hydrogel nano- and micro-particles can be used as potential drug delivery agents.

The release of encapsulated bioactive agents out of the hydrogel particles can be controlled by modifying the microstructure of the hydrogel nanoparticles, or/and by formation of hybrid hydrogel-based drug delivery systems.

In the therapeutic field, hydrogel nanoparticles as described herein can serve as vectors for delivering of hydrophilic and hydrophobic bioactive substances: small drug molecules, as well as high molecular weight biomolecules such as peptides, proteins, siRNA and DNA, as described in further detail hereinbelow. In the diagnostic field, the hydrogel particles described herein can be loaded with imaging agents such as magnetic or gold nanoparticles and serve as a potent biocompatible diagnostic tool for broad range of diseases. The hydrogel nanoparticles described herein can be further utilized in other, non-medicinal applications.

The hydrogel particles can be modified with any type of biological or synthetic molecule to improve stability, efficiency and/or bioavailability, as described in further detail hereinafter.

According to an aspect of some embodiments of the present invention there is provided a composition comprising a plurality of physically discrete hydrogel particles, each hydrogel particle comprising a three-dimensional network made of a plurality of self-assembled peptides and an aqueous medium.

As used herein, the term "hydrogel" describes a fibrous 3D network formed of water-soluble natural or synthetic polymer chains, typically containing more than 80% of an aqueous medium (e.g., water or an aqueous solution) and 20% or less of the polymeric material.

In some embodiments, a hydrogel as described herein contains more than 90% aqueous medium (e.g., water or an aqueous solution), and even more than 95% or about 99% aqueous medium (e.g., water or an aqueous solution), and less than 10% of the polymeric material, or even less than 5% of the polymeric material e.g., about 1% of the polymeric material. By "%" it is meant herein weight percents.

Typically, the aqueous medium is an aqueous solution. In some embodiments, the aqueous medium can be an aqueous dispersion or suspension. For example, an aqueous dispersion of a non-soluble agent (e.g., metallic nanoparticles) represents HNPs as described herein which encapsulate particles of such non-soluble agent.

Herein throughout, the phrases "aqueous solution" and "aqueous medium" are used interchangeably.

As used herein, the phrase "fibrous network" refers to a set of connections formed between a plurality of fibrous components. Herein, the fibrous components are fibrillar structures made of peptides, each formed upon self-assembly of short peptide building blocks as described herein.

As used herein, "physically discrete" means that the nanoparticles are not physically (or chemically) associated to one another, rather, each is an independent body within the composition.

By "hydrogel particles" it is therefore meant that each particle in the composition is a discrete mass in a form of a hydrogel as defined herein.

The hydrogel particles described herein are advantageously small in size, being in the microscale, and, optionally and preferably, in the nanoscale.

In some embodiments, the plurality of hydrogel particles comprises hydrogel microparticles, hydrogel nanoparticles and a combination thereof.

By "hydrogel microparticles" it is meant that at least 50%, or at least 60%, or at least 70%, or at least 80%, or at least 90%, or at least 95%, or at least 98%, or at least 99%, or all of the particles in the composition are microparticles, whereby a "microparticle" is a micron-sized discrete mass in a form of a hydrogel as defined herein, being less than 1 mm in the largest axis thereof (which is referred to herein also as diameter).

By "hydrogel nanoparticles" it is meant that at least 50%, or at least 60%, or at least 70%, or at least 80%, or at least 90%, or at least 95%, or at least 98%, or at least 99%, or all of the particles in the composition are nanoparticles, whereby a "nanoparticle" is a nano-sized discrete mass in a form of a hydrogel as defined herein, whereby each particle is being less than 1 micron in the largest axis thereof (which is referred to herein also as diameter).

Figure 1B:
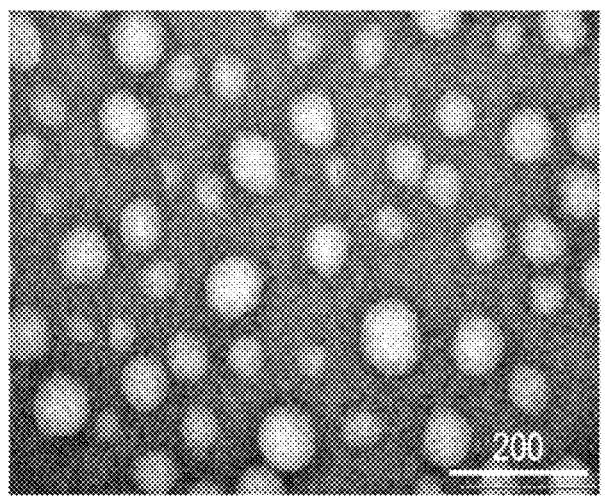
Figure 1C:
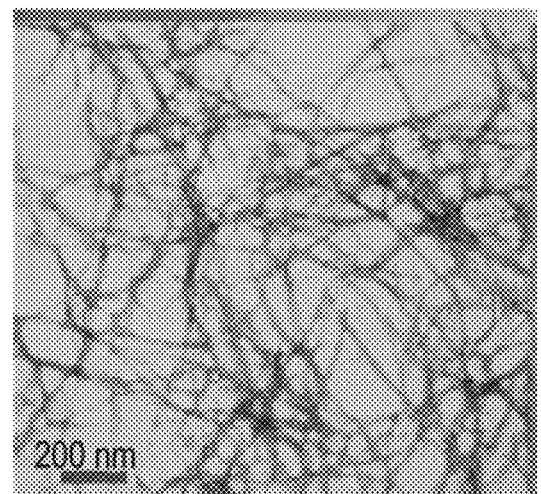

FIGS. 1B and 1C demonstrate the formation of hydrogel nanoparticles from Fmoc-FF, according to some exemplary, non-limiting, embodiments of the present invention, versus hydrogels made of Fmoc-FF under conditions that do not favor nanoparticles formation, as previously disclosed.

As can be clearly seen in FIGS. 1B and 1C, while a fibrous network is present in a hydrogel made of Fmoc-FF (FIG. 1C), discrete particles are present when Fmoc-FF is subjected to conditions which favor nanoparticles formation (FIG. 1B).

In some of any of the embodiments described herein, an average diameter of at least a portion (as defined herein) or of or all of the hydrogel particles in the composition ranges from 1 nm to 1000 nm, or from 1 nm to 500 nm, or from 10 nm to 300 nm, including any value therebetween. Higher values (e.g., in micron-scale) are also contemplated.

In some of any of the embodiments described herein, the size distribution of the hydrogel particles is such that the plurality of particles possesses no more than 6 differently-sized populations of particles, preferably no more than 5, no more than 4, no more than 3 or no more than 2 differently-sized populations of particles.

In exemplary embodiments, the size distribution of the hydrogel particles features 2 main differently-sized populations of particles. In some of these embodiments, one of these populations of particles features an average diameter ranging from 10 nm to 50 nm and one of these populations of particles features an average diameter ranging from about 200 nm to about 250 nm. In some of these embodiments, one of the populations features an average diameter of about 20 nm to 25 nm (e.g., 21-22 nm), and another population feature an average diameter of about 220 nm to about 230 nm (e.g., about 225-226 nm).

Without being bound by any particular theory, it is assumed that the particles follow the known bimodal phenomenon, which is assumed to be attributed to an equilibrium between two opposite processes, droplet fragmentation and droplet re-coalescence. Again, without being bound by any particular theory, it is assumed that equilibrium occurs due to the conditions used for forming the hydrogel nanoparticles, such as a presence and type of a surfactant type and/or a speed of the homogenization, as discussed in further detail hereinafter.

Any other average sizes of two or more differently-sized populations of particles are contemplated, particularly considering the ability to manipulate the particles size and size distribution by means of manipulating process parameters and chemical composition of the precursor peptides.

In some of any of the embodiments described herein, the hydrogel particles are formed of self-assembled peptides.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH$_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

As used herein throughout, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. The term "amino acid" as used herein includes both D- and L-amino acids.

By "self-assembled peptides" it is meant that the peptides forming the hydrogel particles are such that are capable to self-assemble into structures when subjected to suitable environmental conditions. It is to be understood that self-assembly means that the peptides assemble to form ordered structures without being subjected to chemical reactions (e.g., reactions which lead to covalent bond formation).

Previous studies have shown that short peptides having one or more aromatic amino acid residues, as defined hereinunder, self-assemble into ordered structures or hydrogels when diluted in an aqueous solution.

In some of any of the embodiments described herein, the plurality of self-assembled peptides forming the HNPs comprise (or are consisted of) peptides of 2-6 amino acid residues, wherein at least one of the amino acids in each of such peptides is an aromatic amino acid residue. Such peptides are also referred to herein as aromatic peptides.

Thus, herein throughout, the phrase "aromatic peptide" encompasses a plurality of peptides, being the same or different from one another, wherein at least a portion (e.g., 50%, or 60%, or 70%, or 80%, or 90%, or 95%, or 98%, or 99% or all) of the peptides are each independently a peptide of 2-6 amino acid residue, in which at least one of the amino acid residues is an aromatic amino acid residue as described herein.

Each of the aromatic peptides can independently include 1, 2, 3, 4, 5 or 6 aromatic amino acid residues, as described herein.

In some embodiments, each of the peptides in the plurality of peptides is independently an aromatic peptide, as described herein.

In some embodiments, at least 50%, or at least 60%, or at least 70%, or at least 80%, or at least 90%, or at least 95%, or at least 98%, or at least 99% or all of the peptides in the plurality of peptides are the same aromatic peptides, as described in any of the related embodiments herein.

The phrase "aromatic amino acid residue", as used herein, refers to an amino acid residue that has an aromatic moiety in its side-chain.

As used herein, the phrase "aromatic moiety" describes a monocyclic or polycyclic moiety having a completely conjugated pi-electron system. The aromatic moiety can be an all-carbon moiety or can include one or more heteroatoms such as, for example, nitrogen, sulfur or oxygen. The aromatic moiety can be substituted or unsubstituted, whereby when substituted, the substituent can be, for example, one or more of alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine, as defined herein.

Exemplary aromatic moieties include, for example, phenyl, biphenyl, naphthalenyl, phenanthrenyl, anthracenyl, [1,10]phenanthrolinyl, indoles, thiophenes, thiazoles and, [2,2']bipyridinyl, each being optionally substituted. Thus, representative examples of aromatic moieties that can serve as the side chain within the aromatic amino acid residues described herein include, without limitation, substituted or unsubstituted naphthalenyl, substituted or unsubstituted phenanthrenyl, substituted or unsubstituted anthracenyl, substituted or unsubstituted [1,10]phenanthrolinyl, substituted or unsubstituted [2,2']bipyridinyl, substituted or unsubstituted biphenyl and substituted or unsubstituted phenyl. The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine. In some embodiments, one or more of the peptides in the plurality of peptides is an aromatic dipeptide.

In some embodiments, at least a portion (e.g., at least 50%, or at least 60%, or at least 70%, or at least 80%, or at least 90%, or at least 95%, or at least 98%, or at least 99%) or all, of the peptides in the plurality of peptides are aromatic dipeptides, namely, are peptides of 2 amino acid residues, at least one of the amino acid residues being an aromatic amino acid residue as defined herein.

In some embodiments, each peptide in the plurality of peptides is an aromatic dipeptide.

Herein, an aromatic dipeptide describes a peptide composed of two amino acid residues, wherein at least one of these amino acid residues is an aromatic amino acid residue.

The aromatic dipeptides according to any of these embodiments can be the same or different (e.g., the plurality of peptides comprises two or more types of chemically-distinct aromatic dipeptides). When the aromatic dipeptides are different, they can differ from one another by the type of a non-aromatic amino acid residue and/or by the time of the one or two aromatic amino acid residues.

In some of any of the embodiments of the present invention, at least one peptide in the plurality of peptides used for forming the hydrogel is an aromatic dipeptide, comprising two aromatic amino acid residues. In some embodiments, each peptide in the plurality of peptides is an aromatic dipeptide, comprising two aromatic amino acid residues.

Thus, the peptides used for forming the hydrogel can be dipeptides composed of one or two aromatic amino acid residues.

The aromatic amino acid residues composing the dipeptide can be the same, such that the dipeptide is a homodipeptide, or different. Preferably, the hydrogel is formed from aromatic homodipeptides.

Hence, according to the presently most preferred embodiment of the present invention, each peptide in the plurality of peptides used for forming the hydrogel is a homodipeptide composed of two aromatic amino acid residues that are identical with respect to their side-chains residue.

Exemplary aromatic homodipeptide include, but are not limited to, phenylalanine-phenylalanine dipeptide (diphenylalanine peptide), naphthylalanine-naphthylalanine dipeptide, phenanthrenylalanine-phenanthrenylalanine dipeptide, anthracenylalanine-anthracenylalanine dipeptide, [1,10]phenanthrolinylalanine-[1,10]phenanthrolinylalanine dipeptide, [2,2']bipyridinylalanine-[2,2']bipyridinylalanine dipeptide, (pentahalo-phenylalanine)-(pentahalo-phenylalanine) dipeptide, (amino-phenylalanine)-(amino-phenylalanine) dipeptide, (dialkylamino-phenylalanine)-(dialkylamino-phenylalanine) dipeptide, (halophenylalanine)-(halophenyl-alanine) dipeptide, (alkoxy-phenylalanine)-(alkoxy-phenyl-alanine dipeptide, (trihalomethyl-phenylalanine)-(trihalomethyl-phenylalanine) dipeptide, (4-phenyl-phenylalanine)-(4-phenyl-phenylalanine) dipeptide and (nitro-phenylalanine)-(nitro-phenylalanine) dipeptide.

In some of any of the embodiments described herein, the plurality of aromatic dipeptides comprises a plurality of diphenylalanine peptides. In some embodiments, the plurality of aromatic dipeptides consists of diphenylalanine peptides (Phe-Phe, or FF, dipeptides).

In other embodiments, the peptides in the plurality of peptides comprise 2, 3, 4, 5 or 6 amino acid residues, or any combination thereof.

In some embodiments, one or more, or each, of the peptides in the plurality of peptides, comprise, in addition to an aromatic amino acid residue(s), an RGD sequence.

As used herein and in the art, an RGD sequence is a sequence of the amino acid residues Arg-Gly-Asp. Analogs or peptidomimetics, as defined herein, of the RGD sequence are also contemplated.

In some of any of these embodiments, a peptide or peptidomimetic which comprises a RGD sequence consists of an RGD sequence and 1, 2 or 3 additional amino acid residues as described herein, at least one of these amino acid residues being an aromatic amino acid residue, as described herein.

In some embodiments, the peptide comprises an RGD sequence and an aromatic amino acid residue as described herein, such that the peptide is a tetrapeptide.

In an exemplary embodiment, the plurality of peptides comprises, or consists of, peptides having the amino acid sequence FRGD (SEQ ID NO:1).

In any of the embodiments described herein, one or more of the aromatic peptides comprise an end-capped moiety, and can be referred to as an end-capping modified peptide.

The phrase "end-capping modified peptide", as used herein, refers to a peptide which has been modified at the N-(amine) terminus and/or at the C-(carboxyl) terminus thereof. The end-capping modification refers to the attachment of a chemical moiety to the terminus, so as to form a cap. Such a chemical moiety is referred to herein as an end-capping moiety and is typically also referred to herein and in the art, interchangeably, as a peptide protecting moiety or group.

The phrase "end-capping moiety", as used herein, refers to a moiety that when attached to the terminus of the peptide, provides an end-capping (or modified terminus). The end-capping modification typically results in masking the charge of the peptide terminus, and/or altering chemical features thereof, such as, hydrophobicity, hydrophilicity, reactivity, solubility and the like. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

Representative examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denoted herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

Representative examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

Other end-capping modifications of peptides include replacement of the amine and/or carboxyl with a different moiety, such as hydroxyl, thiol, halide, alkyl, aryl, alkoxy, aryloxy and the like, as these terms are defined herein.

In a preferred embodiment of the present invention, some or all of the peptides that comprise the hydrogels are end-capping modified only at the N-terminus (namely, peptides having an end-capping moiety substituting the N-terminus of the peptide).

End-capping moieties can be classified by their aromaticity. Thus, end-capping moieties can be aromatic or non-aromatic.

Representative examples of non-aromatic end capping moieties suitable for N-terminus modification include, without limitation, formyl, acetyl trifluoroacetyl, tert-butoxycarbonyl, trimethylsilyl, and 2-trimethylsilyl-ethanesulfonyl.

Representative examples of non-aromatic end capping moieties suitable for C-terminus modification include, without limitation, amides, allyloxycarbonyl, trialkylsilyl ethers and allyl ethers.

Representative examples of aromatic end capping moieties suitable for N-terminus modification include, without limitation, fluorenylmethyloxycarbonyl (Fmoc). Representative examples of aromatic end capping moieties suitable for C-terminus modification include, without limitation, benzyl, benzyloxycarbonyl (Cbz), trityl and substituted trityl groups.

In a preferred embodiment of the present invention, the end-capping modified peptides are modified by an aromatic (e.g. Fmoc) end-capping moiety.

In some of any of the embodiments described herein, some or all of the peptides forming the hydrogel particles are end-capping modified aromatic Phe-Phe, for example, Fmoc-Phe-Phe (Fmoc-FF). Fmoc-FF has the advantage of being natural, non-toxic, relatively chip, and easy to handle peptide.

In some of any one of the embodiments described herein, some or all of the peptides forming the hydrogel particles are end-capping modified FRGD peptides (SEQ ID NO:1), for example, Fmoc-FRGD peptides (Fmoc-capped peptide having an amino acid sequence as set forth in SEQ ID NO:1).

According to some embodiments, the hydrogel particles are formed upon self-assembling the plurality of aromatic dipeptide in an inverse emulsion, optionally in the presence of an emulsion stabilizer, as described herein.

By "inverted emulsion" it is meant a "water-in-oil" emulsion in which an aqueous phase is dispersed in a continuous oil phase. In some embodiments, the oil phase is an organic solvent whereby the aqueous phase is a solution containing the peptides as described in any of the embodiments herein. The phrases "inverted emulsion" and "inverse emulsion" are used herein interchangeably.

According to some embodiments of the present invention, the composition containing the hydrogel particles further comprises an emulsion stabilizer. In some embodiments, the emulsion stabilizer forms a part of the particles' structure. In some embodiments, the particles are such that the inner portion thereof comprises the peptide-based hydrogel as described herein, and the outer portion thereof comprises the emulsion stabilizer. Other forms of association of the emulsion stabilizer and the hydrogel are also contemplated.

Without being bound by any particular theory, it is assumed that the emulsion stabilizer imparts stability to the hydrogel particles, which otherwise could be subjected to decomposition in an aqueous medium.

An emulsion stabilizer can be, for example, an amphiphilic surfactant. Preferred stabilizers are biocompatible surfactants. An example is a Vitamin A derivative, namely, vitamin A substituted by a hydrophobic moiety, such as vitamin E-TPGS. Other amphiphilic surfactants are also contemplated. Examples include, without limitation, PEG-500 and derivatives thereof (e.g., amine-PEG derivatives), Sorbitan monooleate (Span 80/60/20), sodium dodecylbenzene sulfonate (SDBS), Sodium dodecyl sulfate (SDS) and Sodium lauryl sarcosinate (sarkosyl).

Some or all of the aromatic peptides and/or the end-capping moiety if present therein, can be further modified so as to attach to the hydrogel particles a chemical moiety or an agent that is not inherently present in the dipeptide and/or the end-capping moiety. Such additional moieties or agents can include chemical moieties or groups that may affect surface properties such as hydrophilicity or hydrophobicitiy and/or moieties or agents that may impart a biological effect, such as, for example, therapeutically active agents, targeting moieties, detectable moieties, sensitizers and the like, as is described in further detail hereinunder. These moieties can be covalently attached to the particles, directly or via a spacer, or can be otherwise associated with the hydrogel particles.

In some of any of the embodiments described herein, at least a portion (e.g., 1-100% of the particles, including any intermediate subrange or value therebetween) of the hydrogel particles in the composition have a moiety and/or an agent incorporated therein and/or associated therewith.

By "associated therewith" it is meant that an agent or moiety is in chemical or physical association with the hydrogel particle or a portion thereof.

Thus, for example, agents or moieties can be attached to the external and/or internal surface of the hydrogel particles, by interacting with functional groups present in the hydrogel particles via, e.g., covalent bonds, electrostatic interactions, hydrogen bonding, van der Waals interactions, donor-acceptor interactions, aromatic (e.g., π-π interactions, cation-π interactions and metal-ligand interactions. These interactions lead to the chemical association of the agent or moiety to the hydrogel particle.

As an example, various agents or moieties can be attached to the hydrogel particle via chemical interactions with the side chains, N-terminus or C-terminus of the peptides composing the hydrogel particle and/or with the end-capping moieties, if present.

Alternatively, various agents can be attached to the hydrogel by physical association such as magnetic interactions, surface adsorption, encapsulation, entrapment, entanglement and the likes.

Association (e.g., attachment) of the various agents to the hydrogel can be effected either prior to or subsequent to the hydrogel formation. Thus, for example, an agent or moiety can be attached to one or more of the peptides composing the hydrogel particle prior to the hydrogel formation, resulting in a hydrogel having the agent or moiety attached thereto. Alternatively, an agent or moiety can be attached to surface groups of the hydrogel particle upon its formation.

Encapsulation, entrapment, or entanglement of the various agents is typically effected by forming the hydrogel particles in an emulsion solution containing the encapsulated agent.

Hydrogels entrapping therein a biological or chemical agent can be beneficially utilized for encapsulation and controlled release of the agent.

By "chemical association" it is meant that the agent and/or moiety is bound to the hydrogel particle or a portion thereof via a chemical bond, whereby the chemical bond can be a covalent bond, an ionic bond, hydrogen bond(s), aromatic interactions, and any other chemical bond.

By "physical association" it is meant that the agent and/or moiety is in physical contact with the hydrogel particle. For example the agent/moiety can be deposited on or absorbed to the inner or outer surface of the hydrogel particle or a portion thereof, or can be otherwise incorporated in or on the hydrogel particle.

By "incorporated therein" it is meant that the agent or moiety are incorporated in or absorbed to the inner portion of the hydrogel particle, such that agent or moiety is entrapped within the hydrogel network and/or is within the aqueous medium of the hydrogel particle.

Moieties that can be in association with the hydrogel particles include, for example, chemical moieties or chemical groups, that are attached via chemical or physical association as described herein, to one or more functional groups of the peptide hydrogel.

In some embodiments, a functional group of a side chain of one or more of the amino acid residues of a peptide in the hydrogel particle, pr of a terminus of a peptide is substituted by or conjugated to a chemical moiety or group.

In some embodiments, a functional group of the end-capping moiety of an end-capped peptide in the hydrogel particle is substituted by or conjugated to a chemical moiety or group.

Exemplary chemical moieties include, but are not limited to, surface modifying groups which may alter, for example, the hydrophobicity or hydrophillicilty of a surface of the hydrogel particles, or the biocompatability or biostability.

Such groups include, for example, saturated or unsaturated, cyclic or linear hydrocarbons of 1-30, preferably 4-30, carbon atoms in length, optionally interrupted by one or more heteroatoms. Such moieties can be covalently attached to the peptide by means of a reactive group that can be used to substitute a functional group of the peptide or the end-capping moiety as described herein, or to form a covalent bond with such a functional group, which is chemically compatible therewith.

The term "hydrocarbon" as used herein encompasses moieties such as alkyl, alkylene, cycloalkyl, aryl, as defined herein, and any combination thereof.

Additional exemplary moieties include, but are not limited to, polar groups such as carboxylic acids or aldehydes, which can be attached to functional groups (e.g., via a spacer) of the peptide or end-capping moiety as described herein, or be generated (e.g., by oxidation) from such functional groups, as well as hydroxyl, amide, thiol, thiocarboxy, thioamide, and the like.

Additional chemical moieties include, but are not limited to, any of the reactive or functional groups as described herein.

Converting a functional group inherently present in a peptide as described herein or in an end-capping moiety, if present, to a chemical moiety as described herein, either by substitution, generation or conjugation (directly or via a spacer) can be performed by chemical reactions known in the art.

In some embodiments, the modification to include a chemical moiety as described herein (e.g., by substitution, generation or conjugation (directly or via a spacer) is performed prior to the formation of the hydrogel particle, such that the peptides, or a portion thereof, forming the hydrogel particles are modified and then self-assemble to form the hydrogel particles, as described herein.

It is to be noted that modifying the peptide prior to formation of the hydrogel particles may affect the parameters of formed hydrogel particles, such as, for example, particles size or size distribution, and can be performed in order to manipulate such parameters.

In some embodiments, the modification to include a chemical moiety as described herein (e.g., by substitution, generation or conjugation, directly or via a spacer) is performed subsequent to the formation of the hydrogel particle, such that the hydrogel particles are subjected to modification. Such a modification may result in modifying the surface properties of the hydrogel, for example, in modifying hydrophobicity or hydrophilicity or biocompatability or biostability or any other property of the hydrogel particles, as desired.

In some embodiments, the modification to include a chemical moiety as described herein (e.g., by substitution, generation or conjugation, directly or via a spacer) is performed so as to generate reactive group (which is not inherently present in the hydrogel particle) in the hydrogel particle, whereby the reactive group is used for associating an agent (e.g., an active or bioactive agent) to the hydrogel particle, as described herein. Exemplary such reactive groups can be groups that facilitate chemical attachment (e.g., via covalent, ionic, hydrogen or aromatic interactions) or physical attachment of the agent to the hydrogel particles. Such groups can be selected according to the agent to be attached, by any person skilled in the art. Exemplary such groups include any of the functional groups and reactive groups described herein.

In some of any of the embodiments described herein, at least a portion of the hydrogel particles include an agent in association therewith, as described herein. The agent can be chemically or physically attached to the particle's surface and/or incorporated in the hydrogel particle.

The agent can be an active agent such as, for example, a surface active agent, a surface modifying agent, a bioactive agent, or can include two or more agents of any combination of the foregoing.

Agents that can be beneficially encapsulated in or attached to the hydrogel include, for example, therapeutically active agents, diagnostic agents, biological substances and labeling moieties. More particular examples include, but are not limited to, drugs, cells, proteins, enzymes, hormones, growth factors, nucleic acids, organisms such as bacteria, fluorescence compounds or moieties, phosphorescence compounds or moieties, and radioactive compounds or moieties.

Surface active agents and surface modifying agents can be, for example, derived from chemical compounds that may modify surface properties of the hydrogel particles, as described herein, and thus may impart stability, dispersity, biostability, bioavailability and/or may affect other properties to the composition (e.g., size and size distribution, hydrophobicity, hydrophillicity, etc., as described herein). Such agents include, for example, surfactants as described herein (e.g., Vitamin E derivatives); hydrocarbons as defined herein, being 4-30 carbon atoms in lengths, fatty acids or fatty acyls; carbohydrates; substituted or unsubstituted polyalkylene glycols (PEG), which, when substituted, can include one or more end groups such as, but not limited to, hydroxy, carboxy, alkoxy, amine, amide, hydrazine, thiol, azide, acetylene, acrylate, and any of the reactive/functional groups described herein; maleimide and biotin/strepavidin. In some embodiments, the agent is a bioactive agent, as described herein, and can be, for example, a diagnostic agent or a therapeutically active agent.

In some embodiments, the bioactive agent is a diagnostic agent.

As used herein, the phrase "diagnostic agent" describes an agent that upon administration to a body of a subject exhibits a detectable and/or measurable feature. These include, for example, labeling compounds or moieties, as is detailed hereinunder.

As used herein, the phrase "labeling compound or moiety" describes a detectable moiety or a probe which can be identified and traced by a detector using known techniques such as spectral measurements (e.g., fluorescence, phosphorescence), electron microscopy, X-ray diffraction and imaging, positron emission tomography (PET), single photon emission computed tomography (SPECT), magnetic resonance imaging (MRI), computed tomography (CT) and the like.

Representative examples of labeling compounds or moieties include, without limitation, chromophores, fluorescent agents, phosphorescent agents, contrast agents, radioactive agents, magnetic compounds or moieties (e.g., diamagnetic, paramagnetic and ferromagnetic materials), and heavy metal clusters, as is further detailed hereinbelow, as well as any other known detectable moieties.

While a labeling moiety can be associated with the hydrogel particle, as described herein, in cases where the one or more of the peptides composing the hydrogel particle is an end-capping modified peptide, the end-capping moiety can serve as a labeling moiety per se.

Thus, for example, in cases where the Fmoc group described hereinabove is used as the end-capping moiety, the end-capping moiety itself is a fluorescent labeling moiety.

In another example, wherein the Fmoc described hereinabove further includes a radioactive fluoro atom (e.g., $^{18}F$) is used as the end-capping moiety, the end-capping moiety itself is a radioactive labeling moiety.

Other materials which may be associated with the hydrogel particles include, without limitation, conducting materials, semiconducting materials, thermoelectric materials, magnetic materials, light-emitting materials, biominerals, polymers and organic materials.

Hydrogel particles having a labeling moiety associated therewith can be utilized in a variety of applications, including, for example, tracing and tracking the location of the fibrous networks of the present invention in mechanical devices and electronic circuitry; and tracing, tracking and diagnosing concentrations of the hydrogel particles of the present invention in a living tissue, cell or host.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}Tc$, $^{18}F$, $^{131}I$ and $^{125}I$.

The term "magnetic agent" describes a substance which is attracted to an externally applied magnetic field. These substances are commonly used as contrast media in order to improve the visibility of internal body structures in Magnetic Resonance Imaging (MRI). The most commonly used compounds for contrast enhancement are gadolinium-based. MRI contrast agents alter the relaxation times of tissues and body cavities where they are present, which, depending on the image weighting, can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process.

The term "chemiluminescent agent" describes a substance which emits light as the result of a chemical reaction.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

In some embodiments, the bioactive agent is a targeting agent or moiety.

As used herein and in the art, the phrase "targeting agent or moiety" describes a chemical entity which has an affinity to a bodily site such as, for example, to organs or tissues overexpressing a biomolecule (e.g., receptor, enzyme, hormone), or to organs or tissues which are enriched with a chemical or biological moiety (e.g., hydroxyapetite in bone tissues). A targeting moiety can be, for example, a receptor ligand, an enzyme substrate, a bone targeting moiety, a moiety that enhances blood-brain barrier permeability, antibodies or fragments thereof, including monoclonal antibodies, lipoproteins, hormones and artificial analogs thereof, charged molecules, polysaccharides, peptides, nucleic acids (aptamers), small molecules such as, for example, folic acid, biotin, bisphosphonate, vitamins, avidin and/or strepavidin. In some embodiments, the bioactive agent is a therapeutically active agent.

As used herein, the phrase "therapeutically active agent" describes a chemical substance, which exhibits a therapeutic activity when administered to a subject. These include, as non-limiting examples, inhibitors, ligands (e.g., receptor agonists or antagonists), co-factors, anti-inflammatory drugs (steroidal and non-steroidal), anti-psychotic agents, analgesics, anti-thrombogenic agents, anti-platelet agents, anti-coagulants, anti-diabetics, statins, toxins, antimicrobial agents, anti-histamines, metabolites, anti-metabolic agents, vasoactive agents, vasodilator agents, cardiovascular agents, chemotherapeutic agents, antioxidants, phospholipids, anti-proliferative agents and heparins.

The therapeutically active agent can be a small molecule or a biological substance.

As used herein, the phrase "biological substance" refers to a substance that is present in or is derived from a living organism or cell tissue. This phrase also encompasses the organisms, cells and tissues. Representative examples therefore include, without limitation, cells, amino acids, peptides, proteins, oligonucleotides, nucleic acids, genes, hormones, growth factors, enzymes, co-factors, antisenses, antibodies, antigens, vitamins, immunoglobulins, cytokines, prostaglandins, vitamins, toxins and the like, as well as organisms such as bacteria, viruses, fungi and the like.

Therapeutically active agents that are suitable for use in the context of some embodiments of the present invention can be small molecules or biomolecules, including, without limitation, anti-proliferative agents, chemotherapeutic agents, radiopharmaceuticals, steroids, vitamins, angiogenesis-promoters, angiogenesis inhibitors, drugs, anti-histamines, antimicrobial agents, antidepressants, anti-psychotic agents, anti-hypertensive agents, anti-inflammatory agents, antioxidants, anti-viral agents, anasthial agents, co-factors, cholesterol, fatty acids, bile acids, saponins, hormones, inhibitors, ligands; cytokines, chemokines, chemo-attractants, chemo-repellants, agonists, antagonists, antibodies, antigens, enzymes, co-factors, growth factors, haptens, hormones, and toxins; nucleotide-based substances such as DNA, RNA, oligonucleotides, labeled oligonucleotides, nucleic acid constructs, and antisenses; saccharides, polysaccharides, phospholipids, glycolipids, viruses and cells.

The following provides exemplary, non-limiting, lists of bioactive agents.

Exemplary chemotherapeutic agents include, without limitation, one of the following: an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog.

Non-limiting examples of chemotherapeutic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Representative examples of non-steroidal anti-inflammatory agents that are usable in this context of the present invention include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, flucorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of anesthetic drugs that are suitable for use in context of the present embodiments include lidocaine, bupivacaine, chloroprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in context of the present embodiments include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox$^R$), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilorate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antidepressants usable in context of the present embodiments include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs"), corticotropin-releasing factor (CRF) antagonists, α-adreno-receptor antagonists, NKI-receptor antagonists, 5-HT$_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

Suitable hormones for use in the context of the present invention include, for example, androgenic compounds and progestin compounds.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

Non-limiting examples of angiogenesis-promoters include vascular endothelial growth factor (VEGF) or vascular permeability factor (VPF); members of the fibroblast growth factor family, including acidic fibroblast growth factor (AFGF) and basic fibroblast growth factor (bFGF); interleukin-8 (IL-8); epidermal growth factor (EGF); platelet-derived growth factor (PDGF) or platelet-derived endothelial cell growth factor (PD-ECGF); transforming growth factors alpha and beta (TGF-α, TGF-β); tumor necrosis factor alpha (TNF-β); hepatocyte growth factor (HGF); granulocyte-macrophage colony stimulating factor (GM-CSF); insulin growth factor-1 (IGF-1); angiogenin; angiotropin; and fibrin and nicotinamide.

Non-limiting examples of cytokines and chemokines include angiogenin, calcitonin, ECGF, EGF, E-selectin, L-selectin, FGF, FGF basic, G-CSF, GM-CSF, GRO, Hirudin, ICAM-1, IFN, IFN-γ, IGF-I, IGF-II, IL-1, IL-2, IL-3, IL-4, IL-5, IL-6, IL-7, IL-8, IL-9, IL-10, M-CSF, MIF, MIP-1, MIP-1α, MIP-1β, NGF chain, NT-3, PDGF-α, PDGF-β, PECAM, RANTES, TGF-α, TGF-β, TNF-α, TNF-β, TNF-κ and VCAM-1.

Additional bioactive agents which can be beneficially associated with the hydrogal particle include cytotoxic factors or cell cycle inhibitors, including CD inhibitors, such as p53, thymidine kinase ("TK") and other agents useful for interfering with cell proliferation.

Additional bioactive agents which can be beneficially associated with the hydrogel particle include genetic therapeutic agents and proteins, such as ribozymes, anti-sense polynucleotides and polynucleotides coding for a specific product (including recombinant nucleic acids) such as genomic DNA, cDNA, or RNA. The polynucleotide can be provided in "naked" form or in connection with vector systems that enhances uptake and expression of polynucleotides. These can include DNA compacting agents (such as histones), non-infectious vectors (such as plasmids, lipids, liposomes, cationic polymers and cationic lipids) and viral vectors such as viruses and virus-like particles (i.e., synthetic particles made to act like viruses). The vector may further have attached peptide targeting sequences, anti-sense nucleic acids (DNA and RNA), and DNA chimeras which include gene sequences encoding for ferry proteins such as membrane translocating sequences ("MTS"), tRNA or rRNA to replace defective or deficient endogenous molecules and herpes simplex virus-1 ("VP22").

Additional bioactive agents which can be beneficially associated with the hydrogel particle include gene delivery agents, which may be either endogenously or exogenously controlled. Examples of endogenous control include promoters that are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

Additional bioactive agents which can be beneficially associated with the hydrogel particle include the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Some of these dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Additional bioactive agents which can be beneficially associated with the hydrogel particle include cell survival molecules such as Akt, insulin-like growth factor 1, NF-kB decoys, 1-kB, Madh6, Smad6 and Apo A-1.

Additional bioactive agents which can be beneficially associated with the hydrogel particle include viral and non-viral vectors, such as adenoviruses, gutted adenoviruses, adeno-associated virus, retroviruses, alpha virus (Semliki Forest, Sindbis, etc.), lentiviruses, herpes simplex virus, ex vivo modified cells (i.e., stem cells, fibroblasts, myoblasts, satellite cells, pericytes, cardiomyocytes, skeletal myocytes, macrophage, etc.), replication competent viruses (ONYX-015, etc.), and hybrid vectors, artificial chromosomes and mini-chromosomes, plasmid DNA vectors (pCOR), cationic polymers (polyethyleneimine, polyethyleneimine (PEI) graft copolymers such as polyether-PEI and polyethylene oxide-PEI, neutral polymers PVP, SP1017 (SUPRATEK), lipids or lipoplexes, nanoparticles and microparticles with and without targeting sequences such as the protein transduction domain (PTD).

Any of the active agents described herein can be associated with (e.g., attached to) the hydrogel particle via biostable or biocleavable interactions.

For example, diagnostic agents and targeting agents or moieties are attached to the hydrogel moieties by biostable interactions (e.g., biostable chemical bonds), whereby therapeutically active agents are attached to the hydrogel particle via biocleavable bonds or linking moieties, as defined hereinafter.

Hydrogel particles as described in any one of the embodiments described herein, which include a therapeutically active agent can be used as carriers (e.g., nanocarriers) for delivering the encapsulated agent to a desired bodily site (e.g., organ or tissue). It is assumed that an agent incorporated in a hydrogel particle, as described herein, (e.g., encapsulated in the hydrogel particle) is released from the nanoparticles by diffusion and hence that its release rate can be controlled by manipulating various parameters during preparation of the hydrogel nanoparticles (e.g., porosity, hydrophilicity, hydrophobicity, etc.). Alternatively, or in addition, the agent may be released upon decomposition of the hydrogel particles.

A composition as described herein can be in a form of a solution, a spray or a dry powder.

When in a form of a solution or a spray, the nanoparticles can be used in an appropriate carrier, as described hereinafter. When is a form of a dry powder, nanoparticles which are prepared in an inverted emulsion can be isolated, subjected to lyophilization (freeze-drying), with or without a cryoprotectant.

Thus, in embodiments where the composition is in a form of a dry powder, the composition may further comprise a cryoprotectant.

A cryoprotectant is a substance that is used to protect biological substances (e.g., peptides, proteins, cells) from freezing damage.

Suitable cryoprotectants include, but are not limited to, alcohols such as tert-butanol, 2-Methyl-2,4-pentanediol (MPD), glycerol, glycols, ethylene glycol, propylene glycols, and DMSO.

According to an aspect of some embodiments of the present invention there is provided a process of preparing the composition of the peptide-based NHPs as described in any one of the embodiments herein. The process is generally effected in an inverted emulsion, as defined herein.

In some embodiments, the process comprising:

adding an aqueous solution comprising the plurality of aromatic dipeptides to an organic solution, to thereby form an inverted (water-in-oil) emulsion; and subjecting the emulsion to high speed homogenization.

In some embodiments, the aqueous solution of the aromatic dipeptides is formed by diluting a solution of the plurality of peptides in a water-miscible organic solvent in an aqueous solution.

The peptide concentration upon such a dilution can range from 0.1 mg/ml to 20 mg/ml, or from 1 mg/ml to 20 mg/ml, or from 2 mg/ml to 20 mg/ml, or from 3 mg/ml to 20 mg/ml, or from 4 mg/ml to 20 mg/ml, or from 5 mg/ml to 20 mg/ml, or from 10 mg/ml to 20 mg/ml, or from 1 mg/ml to 10 mg/ml, or from 2 mg/ml to 10 mg/ml, or from 3 mg/ml to 10 mg/ml, or from 4 mg/ml to 10 mg/ml, or from 5 mg/ml to 10 mg/ml, or from 5 mg/ml to 15 mg/ml, including any value or subrange within the indicated ranges.

The phrase "water-miscible organic solvent", as used herein, refers to organic solvents that are soluble or dispersible in water. Examples of water-miscible organic solvents include, without limitation, simple alcohols, such as, methanol, ethanol, 1-propanol, 2-propanol, 1-butanol, 2-butanol, 2-methyl-1-propanol, 2-methyl-2-propanol, 2,2-dimethyl-1-propanol and their halogen substituted analogues, ethylene glycol, acetone, dimethylsulfoxide, acetic acid diethyl ether, tetrahydrofuran etc.

Representative examples of organic solvents include acetone, dimethylsulfoxide (DMSO) and hexafluoroisopropanol (e.g., 1,1,1,3,3,3-hexafluoro-2-propanol, abbreviated herein as HFIP). An exemplary solvent is DMSO.

In some embodiments, only small amounts of the water-miscible organic solvent are used to prepare a solution of the peptides.

The aqueous solution may contain solely water, or may contain additional substances such as buffer salts, emulsifying agents (emulsifiers) which may be required to stabilize the emulsion, surfactants, anti-static agents, chelating agents, preservatives, solubilizers, viscosity modifying agents, biodegradation promoting agents, penetration enhancers and other additional agents as described hereinabove, factors and pharmaceutically acceptable carriers which may be required for the function of the final product.

In an exemplary process, a stock solution of an Fmoc-diphenylalanine dipeptide in DMSO, at concentrations of 25-100 mg/ml is prepared. The stock solution is then further diluted in ultra-pure water under mild conditions to a final peptide concentration as described herein, and is then contacted with an organic solvent or solution, as described herein.

The organic solution can comprise one or more organic solvents and is generally selected as being immiscible with the aqueous solution. Examples of such organic solvents include, without limitation, mineral oil, chloroform, dichloromethane, carbon tetrachloride, methylene chloride, xylene, benzene, toluene, hexane, cyclohexane, diethyl ether and carbon disulfide.

Exemplary mineral oils include, without limitation, silicon oil, white oil, white mineral oil, liquid petrolatum, liquid paraffin or white paraffin oil. The mineral oil vehicle may optionally comprise a mineral oil replacement. Mineral oil replacements include alkanes having at least 10 carbon atoms (e.g., isohexadecane), benzoate esters, aliphatic esters, noncomodogenic esters, volatile silicone compounds (e.g., cyclomethicone), and volatile silicone substitutes. Examples of benzoate esters include $C_{12}C_{15}$ alkyl benzoate, isostearyl benzoate, 2-ethyl hexyl benzoate, dipropylene glycol benzoate, octyldodecyl benzoate, stearyl benzoate, and behenyl benzoate. Examples of aliphatic esters include $C_{12}C_{15}$ alkyl octonoate and dioctyl maleate. Examples of noncomodogenic esters include isononyl isononanoate, isodecyl isononanoate, diisostearyl dimer dilinoleate, arachidyl propionate, and isotridecyl isononanoate. Examples of volatile silicone substitutes include isohexyl decanoate, octyl isononanoate, isononyl octanoate, and diethylene glycol dioctanoate.

The organic and/or the aqueous solution may further include additional agents such as, for example, emulsifying agents (emulsifiers) which may be required to stabilize the emulsion, e.g., as described herein, surfactants, anti-static agents, chelating agents, preservatives, solubilizers, viscosity modifying agents, biodegradation promoting agents, penetration enhancers and other additional agents as described hereinabove.

Buffer salts which are suitable for use in the preparation of the emulsion according to embodiments of the present invention include, but are not limited, to citrate buffers, acetic acid/sodium acetate buffers and phosphoric acid/sodium phosphate buffers.

Emulsifiers which are suitable for use in the preparation of the emulsion according to embodiments of the present invention include, but are not limited, to vegetable derivatives, for example, acacia, tragacanth, agar, pectin, carrageenan and lecithin; animal derivatives, for example, gelatin, lanolin and cholesterol; semi-synthetic agents, for example, methylcellulose and carboxymethylcellulose; and synthetic agents, for example, Carbopols®. Other emulsifiers include glycols and polyglycols, glycerides and polyglycerides, sorbates and polysorbates, sorbitan isostearate, sorbitan oleate, sorbitan sesquioleate, sorbitan trioleate, alkyl-amines and alkyl-amides, and esters, salts and mixtures thereof.

As used herein, the term "surfactant", which is also referred to herein interchangeably as "a surface-active agent" describes a substance that is capable of modifying the interfacial tension of the liquid in which it is dissolved.

Surfactants which are suitable for use in the preparation of the emulsion according to embodiments of the present invention, include anionic, nonionic, amphoteric, cationic and zwitterionic surface-active agents. In general, surfactants can include fatty acid based surfactants; polypeptide based surfactants, for example, proteins, glycoproteins and other modified polypeptides; and polyhydroxyl based surfactants. Specific suitable surface-active agents include but are not limited to triblock copolymer of ethylene oxide (EO) and propylene oxide (PO), (PEO-PPE-PEO), poly(vinyl alcohol) (PVA), acyl glutamates, acyl taurates, N-alkoyl sarcosinates, alkyl alkoxy sulfates, alkyl amidopropyl betaines, alkyl arylsulfonates, alkyl amine oxides, alkyl betaines, alkyl carbonates, alkyl carboxyglycinates, alkyl ether carboxylates, alkyl ether phosphates, alkyl ether sulfates, alkyl ether sulfonates, alkyl glyceryl ether sulfates, alkyl glycinates, alkyl phosphates, alkyl succinates, alkyl sulfates, alkyl sulphosuccinates, ammonium alkyl sulphates, ammonium lauryl sulphate, and derivatives, esters, salts and mixtures thereof.

Suitable solubilizers include, but are not limited to, propylene glycol, 1,3-propylene diol, polyethylene glycol, ethanol, propanol, glycerine, dimethyl sulphoxide, hexylene glycol, propylene carbonate, and derivatives, salts and mixtures thereof.

Suitable viscosity modifiers include, but are not limited to carbomer, polyethylene glycol, polypropylene glycol, sodium xylene sulphonate, urea, acacia, alcohol, ammonium laureth sulfate, ammonium myreth sulfate, amphoteric-12, amphoteric-7, bentonite, butylene glycol, cellulose gum, hydroxyethylcellulose, methylcellulose, hydroxyethyl methylcellulose, hydroxypropyl methylcellulose, cetyl alcohol, and the likes.

In some embodiments, the volume ratio between the aqueous solution containing the peptides and the organic solution ranges from 0.1:100 to 10:100, or from 0.5:100 to 1:50, or from 0.1:100 to 1:100.

In some embodiments, the aqueous solution is added to the organic solution in an amount ranging from 0.1% (v/v) to 10% (v/v), or from 0.5% to 5% (v/v), or from 0.5% to 2% (v/v).

In some embodiments, the homogenization is performed at a speed rate of at least 300 rpm. Preferably, higher speed rates are to be used, in order to obtain smaller particles size and lower size distribution. In some embodiments, the homogenization speed rate is at least 1000, at least 5000, at least 10000, at least 15000, at least 20000 or at least 25000 (e.g., 26000) rpm, including any value there between. Higher speed rates are also contemplated.

In some embodiments, the inverted emulsion further comprises an emulsion stabilizing agent as described herein.

In some embodiments, once the NHPs are formed, isolation of the NHPs is effected by, e.g., filtration, centrifugation or any other method known in the art for separating particles.

In some embodiments a solution of the HNPs is subjected to lyophilization in the presence or absence of a cryoprotecting agent (e.g., tert-butanol), as described herein. HNPs can be first isolated and then re-suspended prior to lyophilization.

The particles average size and size distribution can be manipulated by the choice of the emulsion stabilizer, its concentration, the rate at which homogenization is performed, the choice of cryoprotectant, if present, and its concentration. Further manipulations include the type and concentration of the peptide forming the particles, the aqueous solution to organic solution ratio, the presence of an agent or moiety associated with the particles.

Generally, lower particle size is obtained at higher concentrations of an emulsion stabilizer, and/or of a cryoprotectant, and at higher homogenization rates.

In some embodiments, the self-assembled hydrogel particles are formed in an inverse emulsion in the presence of an agent to be encapsulated (incorporated) therein. Such an agent can be inorganic (e.g., metal particles, organometallic complexes, etc.) or organic (e.g., small molecules, macromolecules, biomolecules, etc.).

In some embodiments, the HNPs further comprise an agent incorporated (encapsulated) therein, and the process further comprises, prior to adding the aqueous solution comprising the peptides to the organic solution, adding the bioactive agent to the aqueous solution comprising the peptides. If the bioactive agent is water-insoluble, it may be added to the solution of the peptides in the water-miscible organic solvent, prior to dilution in the aqueous solution.

As discussed herein, the composition of the peptide-based HNPs can be used in delivering the bioactive agent to a bodily site (e.g., organ or tissue).

The hydrogel particles as described herein allows delivering an active agent via systemic administration (e.g., by injection (intravenous, intraperitoneal, etc.), by inhalation, orally, etc.).

When the bioactive agent is a therapeutically active agent, the composition can be for use in treating a medical condition treatable by the bioactive agent.

When the bioactive agent is a diagnostic agent, the composition can be for use in monitoring a medical condition for which the diagnostic agent is indicative.

Methods of treating a medical condition are also contemplated. Such methods are effected by administering a composition as described herein. The composition can comprise the hydrogel particles as described herein, optionally further comprising a bioactive agent in association therewith, as described herein.

Medical conditions treatable by the composition as described herein can be, for example, medical conditions treatable by the associated bioactive agent.

The bioactive agent can be a small molecule (e.g., a cytotoxic agent, an antibiotic, etc.) or a biological substance, including biomacromolecules such as oligonucleotides or nucleic acids (such that the HNPs encapsulating same can be used for gene therapy), as described herein.

The composition can be administered via various routes of administration, including, but not limited to, intravenous, topical, by inhalation, etc.

In some embodiments, the composition is formulated into a pharmaceutical composition, according to the selected route of administration.

As used herein a "pharmaceutical composition" refers to a preparation of one or more of the active ingredients described herein with other chemical components such as physiologically suitable carriers and excipients. The purpose of a pharmaceutical composition is to facilitate administration of a compound or composition to an organism.

Herein the term "active ingredient" refers to the composition containing the hydrogel particles as described herein, and further comprising a bioactive agent in association with the particles, which exhibits the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered composition. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternatively, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue, brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed herein.

For any of the compositions, methods and uses as described herein, medical conditions which may be monitored and/or treated by means of an active agent as described herein associated with hydrogel particles as described in any one of the embodiments described herein, are determined by the active agent and can be, for non-limiting examples, inflammatory diseases or disorders, viral diseases or disorders, infections associated with a microorganism, proliferative diseases or disorders (e.g., cancer), respiratory diseases or disorders, psychotic diseases or disorders and the like.

Alternatively, compositions as described herein can be formulated into cosmetic or cosmaceutical compositions, using an appropriate carrier.

The beneficial characteristics of the hydrogel particles described herein render them highly suitable for use in various applications. Thus, a composition as described in any one of the embodiments herein can be utilized, for example, for forming an article-of-manufacture, whereby the article-of-manufacture can be, for example, a medicament, a drug delivery system, a cosmetic or cosmaceutical product, an implant, an artificial body part, a tissue engineering and regeneration system, and a wound dressing, as well as various medical devices.

As used herein, the term "medicament" refers to a licensed drug taken to cure or reduce symptoms of an illness or medical condition.

As used herein, the phrase "drug delivery system" refers to a system for transportation of a substance or drug to a specific location, and more specifically, to a desired bodily target, whereby the target can be, for example, an organ, a tissue, a cell, or a cellular compartment such as the nucleus, the mitochondria, the cytoplasm, etc. This phrase also refers to a system for a controlled release of a substance or drug at a desired rate.

As used herein, the term "implant" refers to artificial devices or tissues which are made to replace and act as missing biological structures. These include, for example, dental implants, artificial body parts such as artificial blood vessels or nerve tissues, bone implants, and the like.

As used herein, the phrase "tissue engineering and regeneration" refers to the engineering and regeneration of new living tissues in vitro, which are widely used to replace diseased, traumatized or other unhealthy tissues.

As used herein, the phrase "cosmetic or cosmaceutical products" refers to topical substances that are utilized for aesthetical purposes. Cosmaceutical products typically include substances that further exhibit therapeutic activity so as to provide the desired aesthetical effect. Cosmetic or cosmaceutical products in which the hydrogels, compositions-of-matter and compositions described herein can be beneficially utilized include, for example, products for firming a defected skin or nail, make ups, gels, lacquers, eye shadows, lip glosses, lipsticks, and the like.

Medical devices in which the hydrogels, compositions-of-matter and compositions described herein can be beneficially utilized include, for example, anastomotic devices (e.g., stents), sleeves, films, adhesives, scaffolds and coatings.

In some embodiments, the hydrogel particles as described in any one of the embodiments described herein, which have a bioactive agent associated therewith, as described herein, are used as a delivery system for releasing the active agent upon administration.

The hydrogel particles as described herein as be utilized for preparing medicaments for treating medical conditions as described herein, and/or in methods of delivering agents associated therewith to a bodily site of a subject as described herein.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Whenever a "portion" is referred to herein, it describes any value between 1 to 100% of the entities (e.g., peptides), preferably, at least 10%, 20 5, 30 5, 40%, 50%, 60%, 70%, 80%, 90% or at least 95%, 98%, 99% or all.

The phrase "bioactive agent" is used herein to describe an agent capable of exerting a beneficial activity in a biological system (e.g., a living tissue or organ) of a subject. The beneficial activity includes, for example, a therapeutic activity per se, reduction of adverse side effects induced by another moiety or agent, and/or targeting and/or transportation of another moiety and/or agent towards a desired biological target.

As used herein, the phrase "biocleavable moiety" or "biodegradable moiety" describes a chemical moiety, which undergoes cleavage in a biological system such as, for example, the digestive system of an organism or an enzymatic system in a living cell. Representative examples of biocleavable moieties include, without limitation, amides, carboxylates, carbamates, phosphates, hydrazides, thiohydrazides, disulfides, epoxides, peroxo and methyleneamines. Such moieties are typically subjected to enzymatic cleavages in a biological system, by enzymes such as, for example, hydrolases, amidases, kinases, peptidases, phospholipases, lipases, proteases, esterases, epoxide hydrolases, nitrilases, glycosidases and the like. Alternatively, biocleavable moiety can be an amino acid sequence which specifically cleavable by a certain enzyme.

As used herein, the phrases "functional group" or "reactive group" describe a chemical group that is capable of undergoing a chemical reaction that typically leads to a bond formation. The bond, according to the present invention, is preferably a covalent bond. Chemical reactions that lead to a bond formation include, for example, nucleophilic and electrophilic substitutions, nucleophilic and electrophilic addition reactions, addition-elimination reactions, cycloaddition reactions, rearrangement reactions and any other known organic reactions that involve a reactive group.

Representative examples of functional and/or reactive groups according to the present invention include, without limitation, amine, halide, acyl-halide, sulfonate, sulfoxides, phosphate, hydroxy, alkoxy, aryloxy, thiohydroxy, thioalkoxy, thioaryloxy, cyano, nitro, azo, isocyanate, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine, as these terms are defined hereinabove.

Herein throughout, the phrase "linking moiety" describes a group (a substituent) that is attached to another moiety in the compound via two or more atoms thereof. In order to differentiate a linking group from a substituent that is attached to another moiety in the compound via one atom thereof, the latter will be referred to herein and throughout as an "end group".

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl. Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbam-
ate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxime is an end group, as this phrase is defined hereinabove.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, with R' and R" are as defined herein.

The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(=O)(R')(R") end group or a —P(=O)(R')— linking group, as these phrases are defined hereinabove, with R' and R" as defined herein.

The term "phosphine sulfide" describes a —P(=S)(R')(R") end group or a —P(=S)(R')— linking group, as these phrases are defined hereinabove, with R' and R" as defined herein.

The term "phosphite" describes an —O—PR'(=O)(OR") end group or an —O—PH(=O)(O)— linking group, as these phrases are defined hereinabove, with R' and R" as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and W" are as defined herein.

The term "hydrazine" describes a —NR'—NR"R'" end group or a —NR'—NR"— linking group, as these phrases are defined hereinabove, with R', R", and R'" as defined herein.

The term "silyl" describes a —SiR'R"R'" end group or a —SiR'R"— linking group, as these phrases are defined hereinabove, whereby each of R', R" and R'" are as defined herein.

The term "siloxy" describes a —Si(OR')R"R'" end group or a —Si(OR') R"— linking group, as these phrases are defined hereinabove, whereby each of R', R" and R'" are as defined herein.

The term "silaza" describes a —Si(NR'R")R'" end group or a —Si(NR'R")— linking group, as these phrases are defined hereinabove, whereby each of R', R" and R'" is as defined herein.

The term "silicate" describes a —O—Si(OR')(OR")(OR'") end group or a —O—Si(OR')(OR")— linking group, as these phrases are defined hereinabove, with R', R" and R'" as defined herein.

The term "boryl" describes a —BR'R" end group or a —BR'— linking group, as these phrases are defined hereinabove, with R' and R" are as defined herein.

The term "borate" describes a —O—B(OR')(OR") end group or a —O—B(OR')(O—) linking group, as these phrases are defined hereinabove, with R' and R" are as defined herein.

As used herein, the term "hydrazide" describes a —C(=O)—NR'—NR"R'" end group or a —C(=O)—NR'—NR"— linking group, as these phrases are defined hereinabove, where R', R" and R' are as defined herein.

As used herein, the term "thiohydrazide" describes a —C(=S)—NR'—NR"R'" end group or a —C(=S)—NR'—NR"— linking group, as these phrases are defined hereinabove, where R', R" and R' are as defined herein.

As used herein, the term "epoxide" describes a

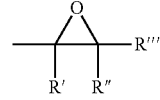

end group or a

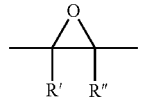

linking group, as these phrases are defined hereinabove, where R', R" and R'" are as defined herein.

As used herein, the term "methyleneamine" describes an —NR'—CH$_2$—CH=CR"R'" end group or a —NR'—CH$_2$—CH=CR"— linking group, as these phrases are defined hereinabove, where R', R" and R' are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Preparation and Characterization of Hydrogel Particles Made of Aromatic Peptides Materials and Methods Materials:
Fmoc-FF was obtained from Bachem (Switzerland)
Fmoc-FRGD (SEQ ID NO:1) was obtained from Bachmen (Switzerland)
Vitamin E-TPGS was obtained from Sigma Aldrich (Israel)
Ultra-pure water was obtained from Biological Industries (Israel)
Mineral oil was obtained from Holland Moran Ltd. (Israel)
DMSO was obtained from Sigma Aldrich (Israel)
PBS was obtained from Biological Industries (Israel)
Uranyl acetate was obtained from (4% w/v) Electron Microscopy Sciences Co.

Hydrogel Particles Preparation—General Procedure:
Generally, peptide-based hydrogel particles (e.g., nanoparticles) are prepared using self-assembly (namely, under conditions that promote self-assembly of the peptide into elongated structures such as fibrillar nanostructures) and modified inverse emulsion techniques. A stock solution of the peptide in an organic solvent is diluted in water, to a final peptide concentration of 5-20 mg/ml (e.g., 10 mg/ml). The aqueous solution is added drop-wise to an organic solution, containing, for example, mineral oil and an emulsion stabilizer (e.g., Vitamin E derivative). The mixture is then subjected to high speed homogenization. Stirring is thereafter continued (e.g., for 2 hours at 4° C.). The formed nanoparticles are then separated from the mixture (e.g., by additional of an organic solvent such as hexane and centrifugation), and dried under reduced pressure.

Freeze-dried peptide-based hydrogel nanoparticles are prepared by suspending the isolated nanoparticles in an aqueous solution (ddH$_2$O), optionally adding to the suspension a cryoprotecting agent (e.g., tert-butanol), mixing (e.g., for 1 hour) and then freezing the suspension and subjecting it to lyophilization.

Fmoc-FF Based Hydrogel Nanoparticles (HNPs) Preparation:
Fmoc-FF-based Hydrogel Nanoparticles (HNPs) were prepared using self-assembly and modified inverse emulsion techniques where vitamin E-TPGS was used an emulsion stabilizer. In brief, a solution of Fmoc-FF in DMSO (100 mg peptide per ml solution) was diluted in ultra-pure water at a final peptide concentration of 10 mg/ml. The resulting solution (0.5 ml) was added drop-wise into 50 ml slightly warmed (about 35° C.) mineral oil containing vitamin E-TPGS at a concentration of 0.4% wt/v (weight/volume) and the obtained mixture was homogenized for 60 seconds using high speed homogenizer, operated, for example, at 26,000 rpm (HOG-020 AC110/220V, 50/60 Hz, MRC Israel). The homogenized mixture was then maintained at 4° C., with continued stirring, for 2 hours, during which self-assembly of the nanoparticles was observed. Upon the completion of the self assembly process, the resulting suspension was mixed with hexane at a concentration of 20% (v/v), and centrifuged to obtain phase separation. Supernatant was removed and the obtained HNPs were washed twice with 1 ml hexane to remove any remaining residues of mineral oil. The HNPs were then vacuum dried for 2 hours in desiccator to remove traces of hexane. The obtained HNPs were used immediately, or stored at 4° C.

Fmoc-FRGD Based HNPs Preparation:
HNPs were prepared from Fmoc-FRGD (Fmoc-capped peptide having an amino acid sequence as set forth in SEQ ID NO:1) as described hereinabove for Fmoc-FF based HNPs, using E-TPGS an emulsion stabilizer, at a concentration of 0.3% w/v or 0.4% w/v.

Nanoparticle Characterization:
Nanoparticles size diameter, polydispersity, and surface charge were measured using ZetaPALS dynamic light scattering (DLS) (Malvern Instruments Ltd. Worcestershire, UK) with appropriate viscosity and refractive index settings. The temperature was maintained at 25° C. during all measurements.

Transmission electron microscopy (TEM) analyses were performed as follows:
A solution of 500 μL HNPs was suspended in PBS and placed on a 400-mesh copper grid. After 2 minutes, the excess of fluid were removed. Negative staining was obtained by covering the grid with 10 μL of 2% uranyl acetate in water. After 2 minutes, excess uranyl acetate solution was removed.

In a comparative TEM analysis, a piece of a hydrogel formed from Fmoc-FF by simple dilution is aqueous solution (without formation of HNPs) was placed on a 400-mesh copper grid and after 1 minute, the piece of the gel and excess fluid were removed. Negative staining was obtained by covering the grid with 10 μL of 2% uranyl acetate in water. After 2 minutes, excess uranyl acetate solution was removed [see, Mahler et al., 2006, supra].

All samples were viewed using a JEOL 1200EX TEM operating at 80 kV.

Experimental Results

Synthesis Parameters:
The formation of HNPs using the Fmoc-FF peptide as a building block is based on the ability of this aromatic peptide to self assemble and form hydrogel with unique mechanical properties, as previously reported.

As shown in FIG. 1A, modified inverse (water-in-oil) emulsion technique was used for HNPs fabrication. In order to formulate the hydrogel nanoparticles, the peptide was first dissolved into its monomeric state in organic solvent (DMSO), followed by dilution in water, and its drop-wise addition into organic phase containing mineral oil and vitamin E-TPGS as an exemplary surfactant (emulsion stabilizer).

The heterogeneous water-in-oil mixture was then subjected to homogenization. The increase in the energy input in the homogenization process allows for the dipeptide mixture to be dispersed and self-assemble into particle aggregates.

In order to promote gelation and allow formation of the surfactant monolayer around the aqueous core of the HNPs, the suspension in then gently stirred for 2 hours at 4° C. Finally, HNPs were purified using centrifugation and a series of washings with hexane. The collected HNPs were re-suspended in water or PBS prior to their characterization.

The physical dimensions of the nanoparticles represent important parameters in NPs design, influencing their biodistribution, clearance kinetics, and in vivo efficacy. Therefore, effective control of the size of HNPs is useful both in basic research and clinical applications.

Herein, the size of HNPs was controlled by optimizing parameters of the emulsion process. One such parameter is the speed rate of homogenization. Since the viscous resistance during the process of homogenization absorbs most of the applied energy, the comminution energy necessary to produce smaller nanoparticles involves additional shear forces. Therefore, to obtained small diameter NPs higher amounts of energy should be applied [Abismail et al. *Ultrason. Sonochem.* 1999, 6, 75-83; Hecht et al. *Langmuir* 2011, 27, 2279-2285]. It was found that desired parameters are obtained when the speed rate of homogenization is 26000 rpm, while higher speed rates can also provide desired parameters.

Another parameter is the volume ratio of the aqueous and organic phase in the emulsion. A suitable range is, for example, 1 ml/100 ml, respectively.

Figure 1D:
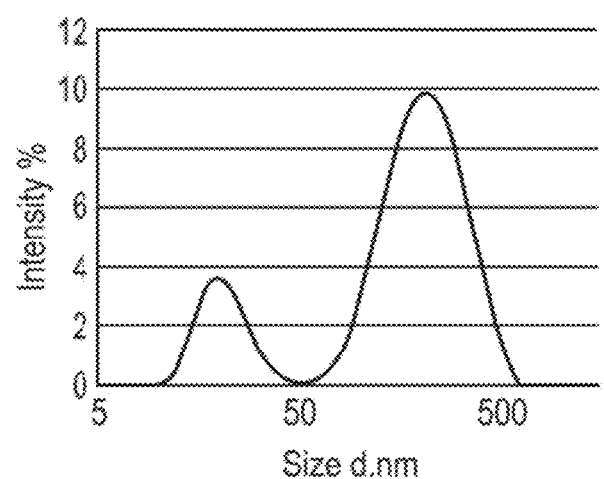
Figure 2A:
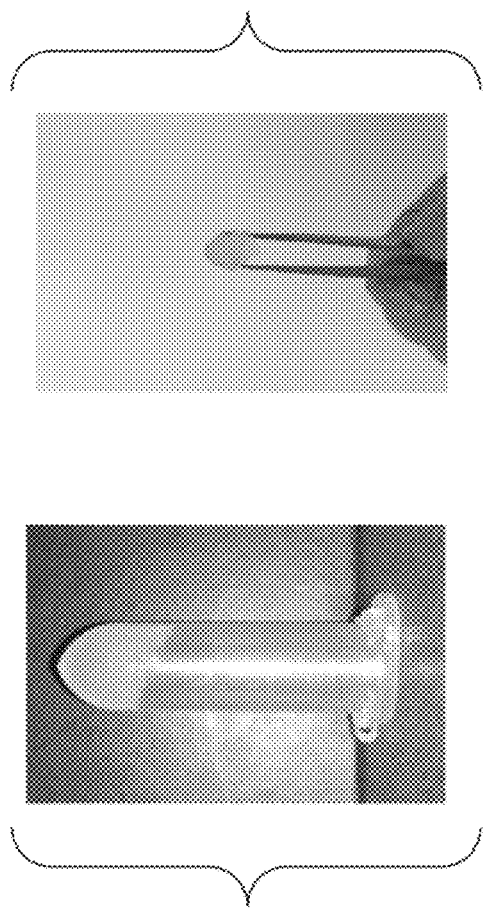
FIGS. 2A-B present Canon PC1732 camera images of aggregated HNPs made of Fmoc-FF, according to some embodiments of the present invention, before being suspended in an aqueous (PBS) solution (FIG. 2A) and TEM images [Image with the magnification of 100 μm is taken by ESEM and the image with magnification of 200 nm is taken by TEM] at two magnifications of the HNPs suspended in PBS (FIG. 2B)
Figure 2B:
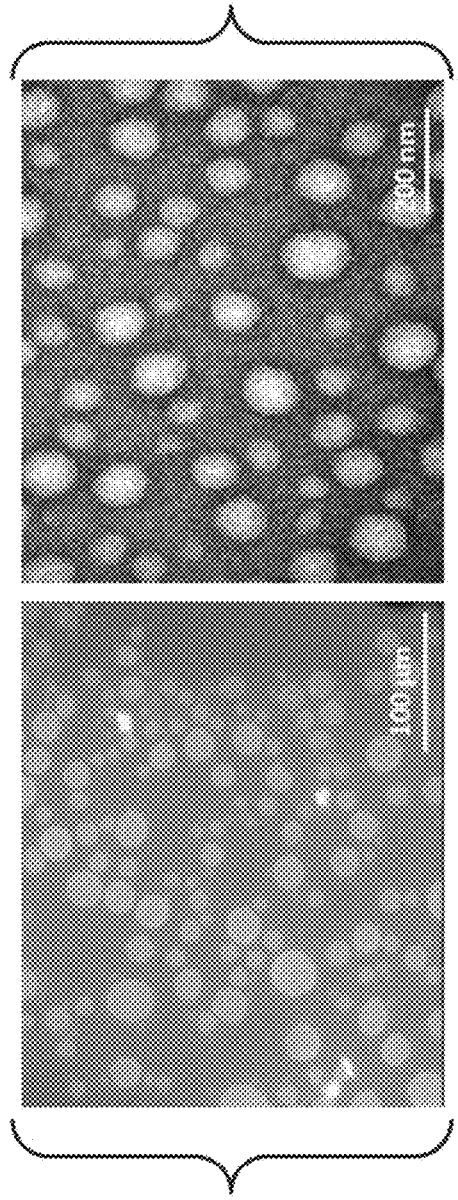

Characterization:

The hydrodynamic size, polydispersity and zeta potential of the obtained HNPs were analyzed using dynamic light scattering (DLS) technique. As shown in FIG. 1D, DLS analysis revealed two distinguishable classes of HNPs with an average size of 21.5±1.3 and 225.9±0.8 nm, respectively.

Transmission electron microscopy (TEM) analysis of the obtained HNPs demonstrated well-defined, discrete spherical structure with a diameter size ranging between 44 and 80 nm (see, FIG. 1B). The different form of self-assembly of the obtained HNPs, compared with hydrogel formed without using inverted emulsion method, can be seen in a comparison to FIG. 1C, which shows a TEM image of background art hydrogel formed from Fmoc-FF, which features a fibirllar network.

Without being bound by any particular theory, it is suggested that the variation between DLS and TEM data is attributed to the swelling of the nanoparticles in the aqueous environment during the DLS analysis, as opposed to the dry environment in the TEM analysis.

The zeta potential values of the HNPs were in average of −25±3 mV. Without being bound by any particular theory, it is suggested that the HNPs' negative charge is due to the presence of carboxyl groups in the peptide building block and/or the coating of the HNPs by the Vitamin E TPGS [Feng et al., 2007, supra].

Figure 3B:
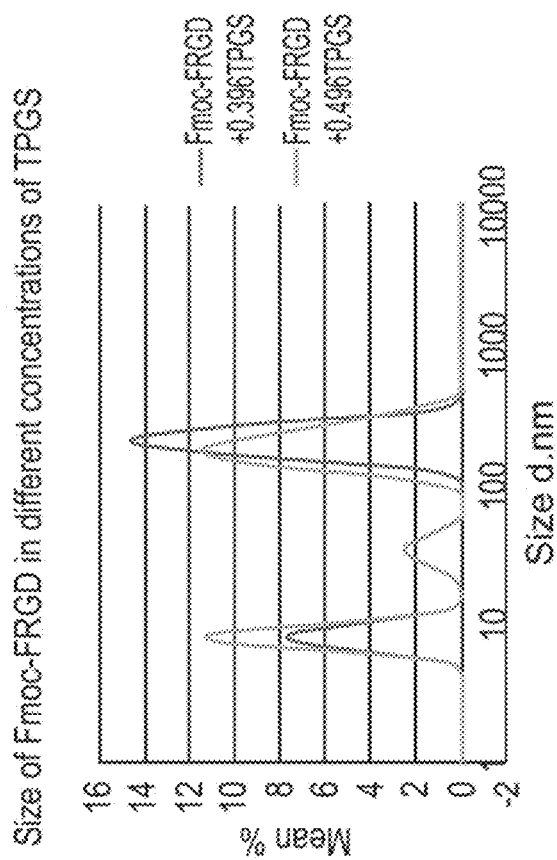
FIGS. 3A-B present a TEM image of exemplary HNPs made of Fmoc-FRGD (Fmoc-capped peptide having an amino acid sequence as set forth in SEQ ID NO:1) by modified inverse emulsion method according to exemplary embodiments of the present invention (FIG. 3A) and comparative plots showing the size distribution of such NHPs when prepared using 0.3% w/v (darker) and 0.4% w/v (lighter) TPGS as an exemplary emulsifier, as measured by dynamic light scattering (DLS) (FIG. 3B).
Figure 3A:
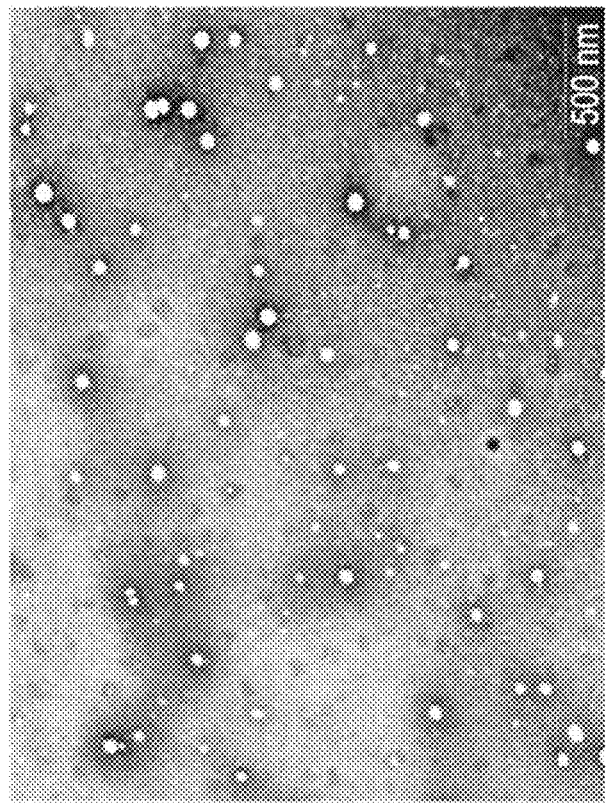

The formation of self-assembled HNPS from another building block, Fmoc-FRGD (Fmoc-capped peptide having an amino acid sequence as set forth in SEQ ID NO:1), was also demonstrated, as shown in FIG. 3A. Stable HNPs were successfully obtained using an E-TPGS as an emulsion stabilizer, at a concentration of 0.3% w/v or 0.4% w/v. The size distribution of the obtained HNPs was similar in both formulations, as can be seen in FIG. 3B.

Example 2

Encapsulation of Gold Nanoparticles by HNPs

Materials and Methods

Materials:
Gold nanoparticles (20 nm in diameter) were obtained from Sigma Aldrich (Israel);
Encapsulation of Gold Nanoparticles:
HNPs encapsulating gold nanoparticles were prepared as described hereinabove in Example 1, while adding hydrophilic inorganic gold nanoparticles to the Fmoc-FF solution (prior to the emulsion formation). Thus, colloidal gold was diluted in water to the final concentration of 100 μl/ml, the Fmoc-FF peptide, dissolved in DMSO was then added to the aqueous solution and the aqueous solution, containing the peptide and the gold nanoparticles was then added to the organic solution and emulsified as described in Example 1 hereinabove. The obtained HNPs were analyzed using TEM.

Experimental Results 20 nm gold nanoparticles dispersed in aqueous solution were used as probes for evaluating the water content in the obtained HNPs. Due to their high contrast in TEM analysis, gold nanoparticles were utilized to visualize the hydrophilic core of HNPs and to practically confirm the ability of HNPs to encapsulate inorganic nanoparticles within the hydrogel matrix.

As can been in FIG. 4A, the hydrophilic colloidal gold nanoparticles are encapsulated inside the HNPs core and are not found outside the particles, in the organic surroundings. FIG. 4B illustrates the encapsulation of gold nanoparticles within the hydrophilic core of HNPs.

Example 3

HNPs Post-Formulation Purification and Storage Stability

Material and Methods

Materials:
tert-Butanol was obtained from Sigma Aldrich (Israel)
Freeze-Dried HNPs Preparation:
A suspension of Fmoc-FF based HNPs in ddH$_2$O was prepared as described in Example 1 hereinabove, without addition of cryoprotectant to the formed suspension, and was thereafter frozen and lyophilized using a bench-top freeze dryer, to thereby obtain the HNPs in a dried powder form.

Freeze-dried preparations were also prepared in the presence of a cryoprotecting agent (e.g., tert-Butanol). An aqueous suspension of HNPs was prepared as described hereinabove, and was thereafter mixed with a 50% (vol/vol) aqueous solution of the cryoprotectant (e.g., tert-Butanol) for 1 hour. The obtained mixture was then rapidly frozen using liquid nitrogen and lyophilized.

Experimental Results

Potential pharmaceutical applications of HNPs require the application of lyophilization method to provide prolonged shelf-life, simplified storage and transportation conditions. However, since the stresses produced by the process of lyophilization may cause aggregation and fusion of HNPs suspension upon freezing and evaporation, cryoprotectants may be added to the HNPs solution to protect their structure from destruction.

The effect of lyophilization, in the presence and absence of a cryoprotecting agent was tested. tert-Butanol was selected as a cryoprotector [Peters-Libeu et al., *Acta Cryst.* 2005, 61, 1065-1068; Cingolani et al., *J. Struct. Biol.* 2002, 139, 46-54].

Figure 5A:
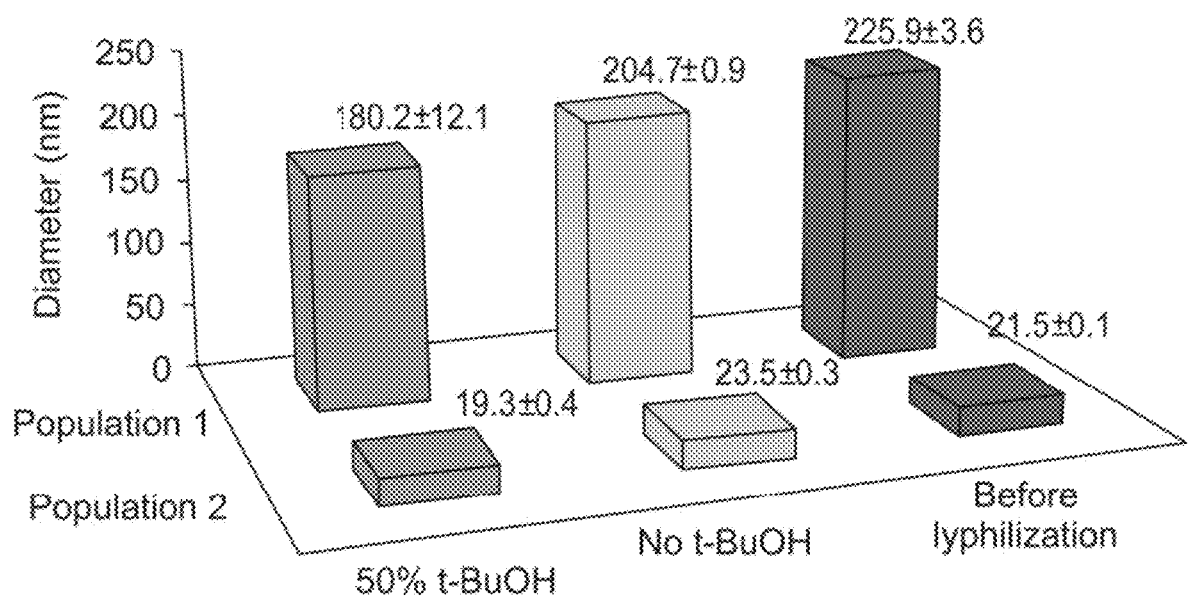
FIGS. 5A-B present data obtained by DLS for exemplary HNPs according to some embodiments of the present invention, made of Fmoc-FF before freeze-drying, after freeze-drying and after-freeze drying in the presence of tert-butanol as a cryoprotecting agent (FIG. 5A), and TEM images of exemplary HNPs according to some embodiments of the present invention, made of Fmoc-FF, re-suspended after freeze-drying in the presence (left image) and absence (right image) of tert-butanol (FIG. 5B)
Figure 5B:
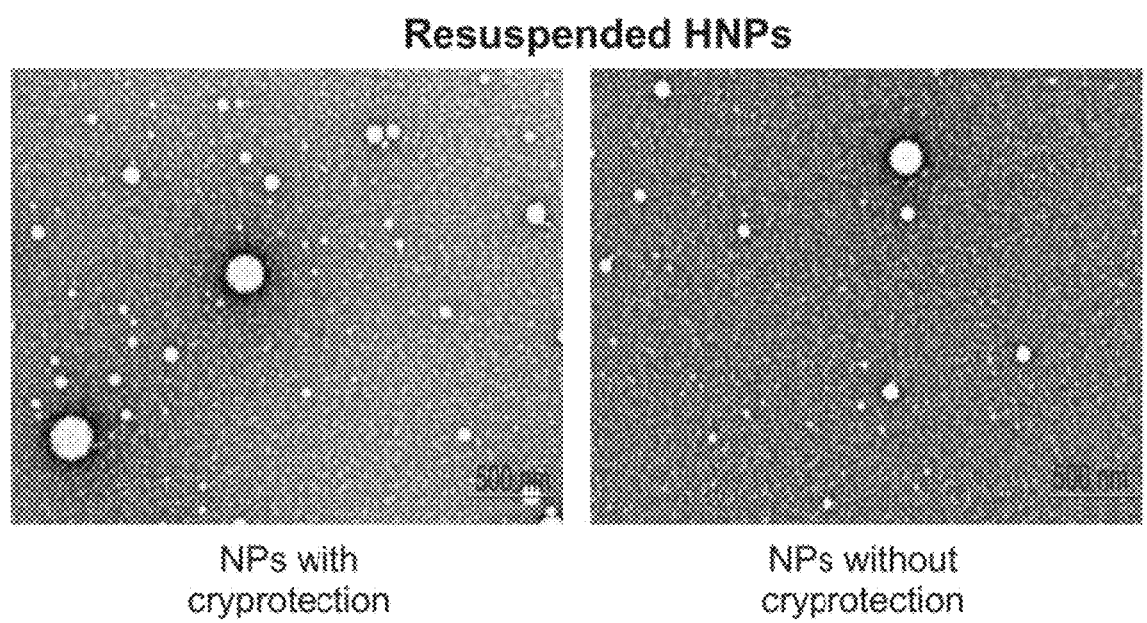

The obtained data is presented in FIGS. 5A-B. Prior to lyophilization, the HNPs two populations had a mean particle diameter of 21.5±1.3 and 225.9±0.8 nm. As shown therein, after freeze-drying, HNPs lyophilized in the presence of tert-Butanol resulted in complete recovery in appropriative aqueous medium and exhibited the same ultrastructural morphology and size distribution. HNPs lyophilized without the tert-Butanol have similar diameters and morphology as to the cryoproctored HNPs with only slight variations between the samples.

These results indicate that the HNPs could be readily turned into powder form, and re-suspended again prior use. In addition, HNPs could be freeze-dried without cryoprotectants.

Without being bound by any particular theory, it is suggested that the need to use separate cryoprotectant is avoided due to the presence of vitamin E-TPGS, which possibly also serves as a stabilization agent and not only as surfactant upon freeze-drying [Feng et al. 2007, supra].

Example 4

Drug Encapsulation and In Vitro Release

Materials and Methods

Materials:
Doxorubicin (Dox) was obtained from Sigma Aldrich Israel Ltd. (Israel)
5-Fluorouracil (5-FU) was obtained from Sigma Aldrich (Israel)
Hank's buffered saline (HBS, pH=7.4) was obtained from Biological Industries (Israel)
Preparation of Drug-Containing HNPs:
For preparation of drug containing HNPs, Dox or 5-Fluorouracil (5-Fu) were dissolved in Fmoc-FF/DMSO solution at a final concentration of 5% wt/wt drug to peptide and the solution was emulsified as described in Example 1 hereinabove.
Confocal Microscopy:
To visualize the encapsulation of doxorubicin (Dox) by the HNPs the sample of Dox loaded HNPs were placed on a specimen slide, and viewed under Zeiss LSM 510 confocal microscope. The fluorescence emission spectrum of Dox (Excitation/Emission, 540 nm/600 nm) allowed it to be visualized in the red channel.
High Performance Liquid Chromatography (HPLC):
HPLC measurements were performed using UltiMate® 3000 system (Dionex) equipped with 3000 pump, and VWD-3000 UV-Vis detector, and Chromeleon® 6.80 software was used. The column used was LiChroCART® 250× 4.6 mm Purospher® STAR (5 µm)C-18 RP (reverse phase). Chromatographic conditions: flow: 1.0 ml/min, linear water (buffer A)/acetonitrile (ACN) (buffer B) gradient (buffer A—100% water, 0.1% TFA; buffer B—100% ACN, 0.1% TFA), with retention time of 7.8 minutes for 5-FU and 14.8 minutes for Dox.
In Vitro Drug Release from NPs:
Drug containing HNPs were suspended in 1 ml Hank's buffered saline (HBS, pH=7.4). The mixture was placed in a dialysis membrane with a molecular weight cut-off of 12-14 kDa; the dialysis membrane was placed in 22 ml of HBS at 37° C. and dialyzed while gently stirring. At predetermine time intervals, 22 ml of solution outside the dialysis bag were replaced with 22 ml fresh HBS and tested at 480 nm for Dox and 265 for 5-Fu using high speed performance liquid chromatography (HPLC), as described herein. The change in the concentration of Dox and 5-Fu was obtained from calibration curve of Dox in HBS.

Experimental Results

The exemplary HNPs as described herein were tested for encapsulation and sustained release of two widely used chemotherapeutics with distinct chemical structures, molecular weights and hydrophobicity: doxorubicin (Dox) and 5-fluorouracil (5-Fu).

The inherent fluorescence of Dox molecule was used to validate its encapsulation in HNPs. As shown in FIG. 6A, the red fluorescence of doxorubicin reveals its presence inside HNPs.

The drug loading efficiency and release kinetics of Dox-loaded and 5-Fu-loaded HNPs were determined by dialysis in HBS at 37° C. under gentle stirring, to mimic physiological conditions.

The change in the concentration of Dox and 5-Fu was deduced from a calibration curve of Dox and 5-Fu in HBS. The release kinetics and the half-lives of the drugs were calculated by fitting the data with an exponential decay model using Origin software with $R^2=0.977$ for Dox and $R^2=0.994$ for 5-Fu.

Figure 6B:
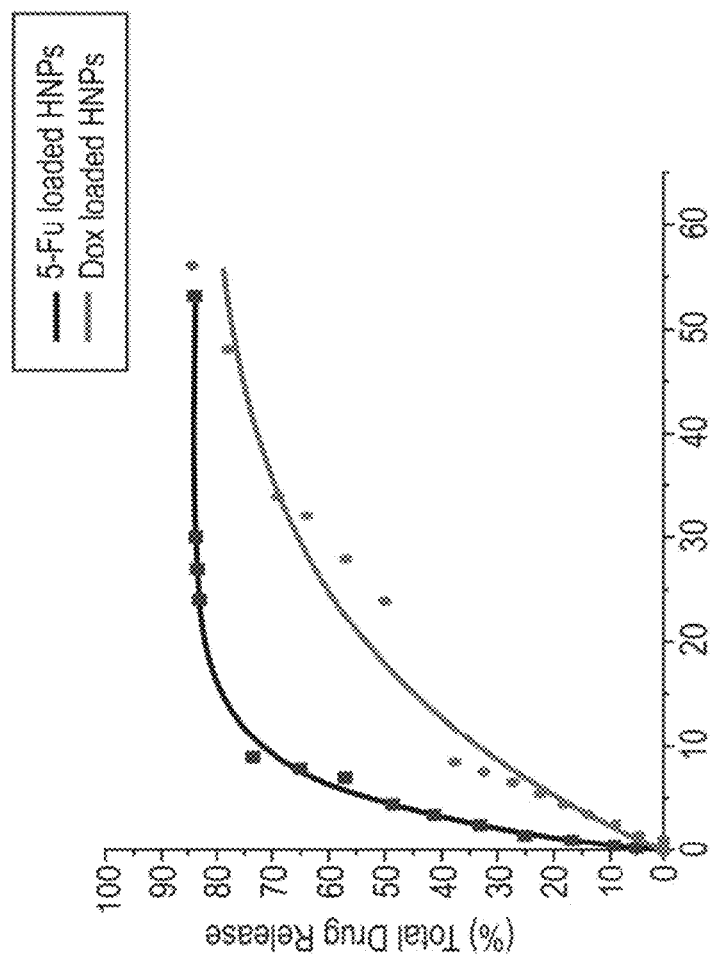
FIGS. 6A-B present confocal microscopy of exemplary NHPs made of Fmoc-FF according to some embodiments of the present invention, encapsulating doxorubicin (FIG. 6A), and comparative plots showing the release profiles of doxorubicin (red) and 5-FU (black) encapsulated in exemplary HNPs according to some embodiments of the present invention, at 37° C. in HBS, as measured by HPLC (FIG. 6B)
Figure 6A:
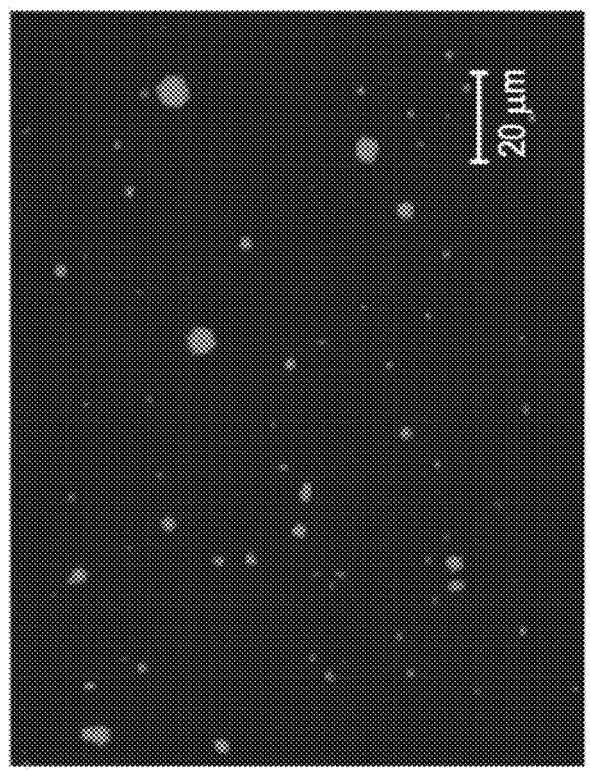

The resulting release profiles of Dox and 5-Fu are presented in FIG. 6B. As can be seen therein, the release profile of 5-Fu-loaded nanoparticles differs from that of the Dox-loaded nanoparticles.

For the 5-Fu-loaded HNPs approximately 50% and 75% of the drug were released within 5 and 12 hours, respectively, after which the kinetics of release reaches plateau.

Dox release from the HNPs matrixes was relatively slower, such that 50% release of the drug was reached only after 20 hours, with 80% release within 55 hours.

Without being bound by ant particular theory, it is suggested that the differences in release kinetics between 5-Fu and Dox is attributed to their dissimilar chemical structural characteristics, while considering that aromatic interactions and hydrogen bond formation between the peptide building block and the drug may play a crucial role in drug encapsulation. Dox molecular structure contains extended aromatic system, compared to 5-Fu, and hence it may be assumed that the Dox aromatic system interacts with the aromatic moieties of Fmoc-FF more efficiently than 5-Fu, and that these interactions account for the Dox extended release [Mart et al., R. *Soft Matter* 2006, 2, 822-835]. In addition, the molecular weight of 5-FU (130 grams/mole) is much lower than the MW of Dox (580 grams/mole). Due to the high water content of HNPs (more than 99%), it may be assumed that the release rate of low molecular weight drugs is only mildly controlled and drug's diffusion through HNPs matrix is much faster with noticeable burst release.

Example 5

Biomolecule Encapsulation

Materials and Methods

Figure 7:
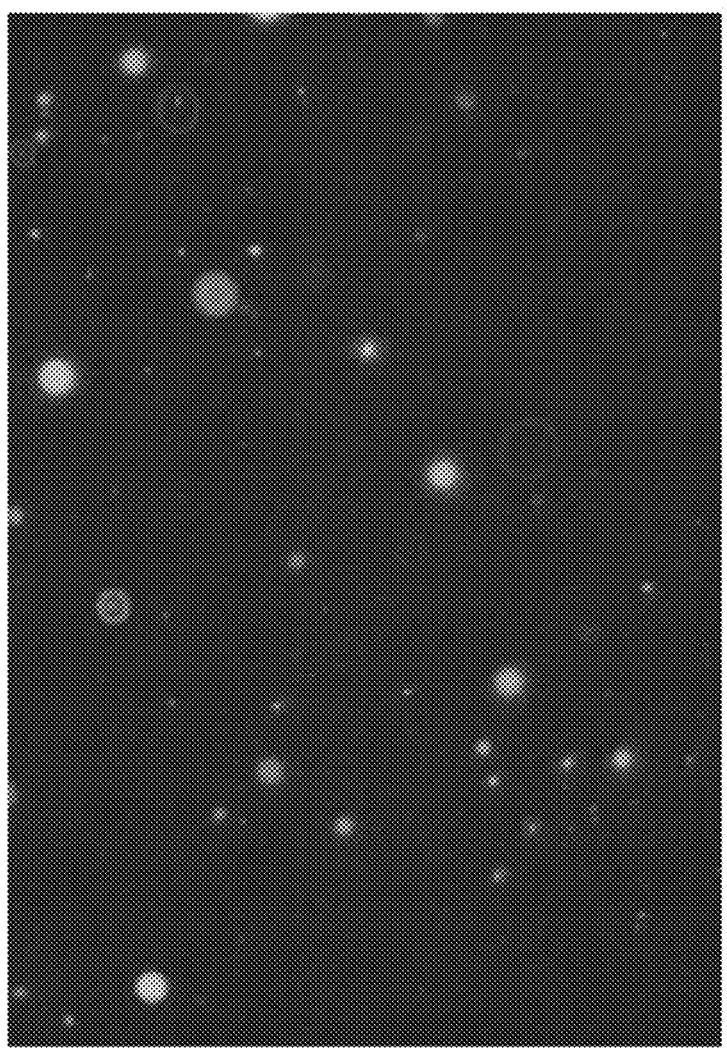
FIG. 7 presents a fluorescent image of exemplary NHPs according to some embodiments of the present invention, made of Fmoc-FF and encapsulating FITC-labeled ds-DNA.

Materials:
FITC-labeled double stranded DNA (P21 RE53; 32 base pairs) was obtained from HyLabs (Israel).
Preparation of Drug-Containing HNPs:
The fluorescent-labeled double stranded DNA was dissolved in DDW at a concentration of 3 µg/ml. A stock solution of Fmoc-FF as described in Example 1 hereinabove was added to the DNA/water solution at a final concentration of 1% peptide. The obtained solution was then subjected to inverted emulsion method as described in Example 1 hereinabove.
FIG. 7 presents a fluorescent image of the obtained HNPs, taken by Nikon Eclipse Ti florescence microscopy. The green fluorescence of the FITC is indicative of the presence of the DNA within the obtained HNPs.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising a plurality of physically discrete hydrogel particles, each hydrogel particle comprising a three-dimensional network made of a plurality of self-assembled peptides and an aqueous medium, wherein each peptide in the plurality of peptides is Phe-Phe, Phe-Gly, naphthylalanine-naphthylalanine (Nal-Nal) or Phe-Arg-Gly-Asp (SEQ ID NO:1),
and wherein each peptide in the plurality of peptides comprises an aromatic end-capping moiety substituting the N-terminus thereof, said end-capping moiety being 9-fluorenylmethyloxycarbonyl (Fmoc),
wherein an average diameter of each of the hydrogel particles ranges from 10 nm to 1000 nm, or from 10 nm to 500 nm,
and wherein the composition further comprises an emulsion stabilizer being in association with the hydrogel particles.

2. The composition of claim 1, wherein the plurality of peptides comprises a plurality of dipeptides.

3. The composition of claim 2, wherein each peptide in the plurality of dipeptides is an aromatic-homodipeptide.

4. The composition of claim 3, wherein the plurality of aromatic dipeptides comprises a plurality of diphenylalanine peptides.

5. The composition of claim 1, wherein each peptide in the plurality of peptides comprises an RGD sequence.

6. The composition of claim 1, wherein the plurality of peptides comprises a plurality of diphenylalanine peptides having said end-capping moiety substituting the N-terminus thereof.

7. The composition of claim 6, wherein each of the diphenylalanine peptides is an Fmoc-diphenylalanine (Fmoc-FF) peptide.

8. The composition of claim 1, wherein the plurality of peptides comprises a plurality of peptides having an FRGD sequence as set forth in SEQ ID NO:1 and said end-capping moiety substituting the N-terminus thereof.

9. The composition of claim 1, wherein the emulsion stabilizer is a Vitamin E derivative.

10. The composition of claim 1, wherein at least a portion of the hydrogel particles have a moiety or an agent incorporated therein and/or associated therewith.

11. The composition of claim 1, being is a form of a dry powder.

12. The composition of claim 11, further comprising a cryoprotectant.

13. The composition of claim 1, further comprising a pharmaceutically acceptable carrier.

14. A process of preparing the composition of claim 1, the process comprising:
adding an aqueous solution comprising the plurality of peptides to an organic solution, to thereby form an inverted (water-in-oil) emulsion; and
subjecting the emulsion to high speed homogenization.

15. The process of claim 14, wherein the homogenization is performed at a speed rate of at least 10,000 rpm.

16. The process of claim 14, wherein the inverted emulsion further comprises an emulsion stabilizing agent.

17. The process of claim 16, wherein the emulsion stabilizing agent is a vitamin E derivative.

18. The process of claim 14, further comprising subjecting the hydrogel particles to lyophilization.

19. The process of claim 18, wherein the lyophilization is effected in the presence of a cryoprotecting agent.

20. The process of claim 14, wherein the hydrogel particles further comprise a bioactive agent incorporated therein, the process further comprising, prior to adding the aqueous solution of peptides to the organic solution, adding the bioactive agent to the aqueous solution of the peptides.

21. A method of delivering a bioactive agent to a bodily organ or tissue, the method comprising administering to the subject the composition of claim 10, wherein the moiety or agent incorporated therein and/or associated therewith is a bioactive agent.

22. The method of claim 21, wherein the delivering is effected via systemic administration.

23. The method of claim 21, wherein the bioactive agent is a therapeutically active agent, the method being for treating a medical condition treatable by the bioactive agent.

24. The method of claim 21, wherein the bioactive agent is a diagnostic agent, the method being for monitoring a medical condition for which the diagnostic agent is indicative.

* * * * *